United States Patent
Watson et al.

(10) Patent No.: US 8,894,643 B2
(45) Date of Patent: Nov. 25, 2014

(54) INTEGRAL ELECTRODE PLACEMENT AND CONNECTION SYSTEMS

(75) Inventors: John Paul Watson, San Jose, CA (US);
Edmund Tam, Mountain View, CA (US); Vahid Saadat, Atherton, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1232 days.

(21) Appl. No.: 12/778,907

(22) Filed: May 12, 2010

(65) Prior Publication Data

US 2010/0262140 A1  Oct. 14, 2010

Related U.S. Application Data

(63) Continuation-in-part of application No. 12/575,674, filed on Oct. 8, 2009, now Pat. No. 8,333,012.

(60) Provisional application No. 61/177,619, filed on May 12, 2009, provisional application No. 61/104,650, filed on Oct. 10, 2008.

(51) Int. Cl.
*A61B 18/18* (2006.01)
*A61B 1/313* (2006.01)
(Continued)

(52) U.S. Cl.
CPC ............... *A61B 1/018* (2013.01); *A61B 1/3137* (2013.01); *A61B 1/012* (2013.01); *A61B 1/00087* (2013.01); *A61N 1/05* (2013.01); *A61B 1/00089* (2013.01); *A61B 1/0008* (2013.01); *A61B 1/05* (2013.01); *A61N 1/06* (2013.01)
USPC .......................................................... 606/41

(58) Field of Classification Search
CPC ............... A61B 1/00089; A61B 18/14; A61B 18/1492; A61B 2018/00065; A61B 2018/00107; A61B 2018/0016; A61B 2018/00166; A61B 2018/00172; A61B 2018/00184; A61B 2018/00214; A61B 2018/00577; A61B 2018/00964; A61B 2018/00982; A61B 2018/00994; A61B 2018/1475
USPC ....................................................... 606/41–45
See application file for complete search history.

(56) References Cited

U.S. PATENT DOCUMENTS 2,305,462 A   12/1942  Wolf
3,874,388 A    4/1975  King et al.
(Continued)

FOREIGN PATENT DOCUMENTS

DE   10028155 A1   12/2000
EP    0283661      9/1988
(Continued)

OTHER PUBLICATIONS

U.S. Appl. No. 11/259,498, filed Oct. 25, 2005 in the name of Saadat, Notice of Allowance mailed Nov. 15, 2010.
(Continued)

*Primary Examiner* — Linda Dvorak
*Assistant Examiner* — Amanda Scott

(57) ABSTRACT

Electrode placement and connection systems are described which allow for the electrical connection and maintenance of one or more electrodes positioned on a substrate which is subjected to a variety of mechanical stresses. Electrodes may also be formed on flexible circuit assemblies integrated within or along the hood. The circuit assemblies may also provide structural support to the hood during delivery and/or deployment. Such a system may include an imaging hood having an aperture through which transparent fluid is flowed and one or more electrodes positioned along or about the hood. As the hood is configured between a low-profile and opened configuration, these electrodes may remain electrically coupled despite the mechanical stresses subjected to the electrodes and the connections thereto.

11 Claims, 32 Drawing Sheets

(51) Int. Cl.
*A61B 1/00* (2006.01)
*A61B 1/05* (2006.01)
*A61B 1/018* (2006.01)
*A61N 1/06* (2006.01)
*A61B 1/012* (2006.01)
*A61N 1/05* (2006.01)

(56) References Cited

U.S. PATENT DOCUMENTS

| | | | |
|---|---|---|---|
| 4,569,335 A | 2/1986 | Tsuno | |
| 4,576,146 A | 3/1986 | Kawazoe et al. | |
| 4,615,333 A | 10/1986 | Taguchi | |
| 4,619,247 A | 10/1986 | Inoue et al. | |
| 4,676,258 A | 6/1987 | Inokuchi et al. | |
| 4,681,093 A | 7/1987 | Ono et al. | |
| 4,727,418 A | 2/1988 | Kato et al. | |
| 4,848,323 A | 7/1989 | Marijnissen et al. | |
| 4,911,148 A | 3/1990 | Sosnowski et al. | |
| 4,957,484 A | 9/1990 | Murtfeldt | |
| 4,991,578 A | 2/1991 | Cohen | |
| 4,998,916 A | 3/1991 | Hammerslag et al. | |
| 5,057,106 A | 10/1991 | Kasevich et al. | |
| 5,195,969 A * | 3/1993 | Wang et al. | 604/96.01 |
| 5,277,201 A * | 1/1994 | Stern | 607/98 |
| 5,330,496 A | 7/1994 | Alferness | |
| 5,334,159 A | 8/1994 | Turkel | |
| 5,336,252 A | 8/1994 | Cohen | |
| 5,339,800 A | 8/1994 | Wiita et al. | |
| 5,385,148 A | 1/1995 | Lesh et al. | |
| 5,405,376 A | 4/1995 | Mulier et al. | |
| 5,421,338 A | 6/1995 | Crowley et al. | |
| 5,505,730 A * | 4/1996 | Edwards | 606/41 |
| 5,515,853 A | 5/1996 | Smith et al. | |
| 5,558,619 A | 9/1996 | Kami et al. | |
| 5,575,756 A | 11/1996 | Karasawa et al. | |
| 5,575,810 A | 11/1996 | Swanson et al. | |
| 5,695,448 A | 12/1997 | Kimura et al. | |
| 5,713,946 A | 2/1998 | Ben-Haim | |
| 5,716,321 A | 2/1998 | Kerin et al. | |
| 5,749,846 A | 5/1998 | Edwards et al. | |
| 5,749,890 A | 5/1998 | Shaknovich | |
| 5,873,815 A | 2/1999 | Kerin et al. | |
| 5,895,417 A | 4/1999 | Pomeranz et al. | |
| 5,897,487 A | 4/1999 | Ouchi | |
| 5,908,445 A | 6/1999 | Whayne et al. | |
| 5,925,038 A * | 7/1999 | Panescu et al. | 606/41 |
| 5,941,845 A | 8/1999 | Tu et al. | |
| 5,944,690 A | 8/1999 | Falwell et al. | |
| 5,964,755 A | 10/1999 | Edwards | |
| 5,971,983 A | 10/1999 | Lesh | |
| 6,004,269 A | 12/1999 | Crowley et al. | |
| 6,086,534 A | 7/2000 | Kesten | |
| 6,112,123 A | 8/2000 | Kelleher et al. | |
| 6,129,724 A | 10/2000 | Fleischman et al. | |
| 6,139,508 A | 10/2000 | Simpson et al. | |
| 6,167,297 A | 12/2000 | Benaron | |
| 6,174,307 B1 | 1/2001 | Daniel et al. | |
| 6,258,083 B1 | 7/2001 | Daniel et al. | |
| 6,306,081 B1 | 10/2001 | Ishikawa et al. | |
| 6,315,778 B1 | 11/2001 | Gambale et al. | |
| 6,396,873 B1 | 5/2002 | Goldstein et al. | |
| 6,428,536 B2 | 8/2002 | Panescu et al. | |
| 6,458,151 B1 | 10/2002 | Saltiel | |
| 6,475,223 B1 | 11/2002 | Werp et al. | |
| 6,482,162 B1 | 11/2002 | Moore | |
| 6,514,248 B1 * | 2/2003 | Eggers et al. | 606/41 |
| 6,532,380 B1 | 3/2003 | Close et al. | |
| 6,587,709 B2 | 7/2003 | Solf et al. | |
| 6,605,055 B1 | 8/2003 | Sinofsky et al. | |
| 6,613,062 B1 | 9/2003 | Leckrone et al. | |
| 6,626,855 B1 | 9/2003 | Weng et al. | |
| 6,635,070 B2 | 10/2003 | Leeflang et al. | |
| 6,704,043 B2 | 3/2004 | Goldstein et al. | |
| 6,751,492 B2 | 6/2004 | Ben-Haim | |
| 6,755,811 B1 | 6/2004 | Constantz | |
| 6,773,402 B2 | 8/2004 | Govari et al. | |
| 6,780,151 B2 | 8/2004 | Grabover et al. | |
| 6,858,005 B2 | 2/2005 | Ohline et al. | |
| 6,863,668 B2 | 3/2005 | Gillespie et al. | |
| 7,019,610 B2 | 3/2006 | Creighton, IV et al. | |
| 7,025,746 B2 | 4/2006 | Tal | |
| 7,090,683 B2 | 8/2006 | Brock et al. | |
| 7,186,214 B2 | 3/2007 | Ness | |
| 7,309,328 B2 | 12/2007 | Kaplan et al. | |
| 7,435,248 B2 | 10/2008 | Taimisto et al. | |
| 7,534,204 B2 | 5/2009 | Starksen et al. | |
| 7,569,052 B2 | 8/2009 | Phan et al. | |
| 7,736,347 B2 | 6/2010 | Kaplan et al. | |
| 7,758,499 B2 | 7/2010 | Adler | |
| 7,828,797 B2 * | 11/2010 | Eggers | 606/46 |
| 7,860,555 B2 | 12/2010 | Saadat | |
| 7,860,556 B2 | 12/2010 | Saadat | |
| 8,295,902 B2 * | 10/2012 | Salahieh et al. | 600/374 |
| 8,500,732 B2 * | 8/2013 | Truckai et al. | 606/41 |
| 2001/0039416 A1 | 11/2001 | Moorman et al. | |
| 2001/0047184 A1 | 11/2001 | Connors | |
| 2002/0004644 A1 | 1/2002 | Koblish | |
| 2002/0026145 A1 | 2/2002 | Bagaoisan et al. | |
| 2002/0087166 A1 | 7/2002 | Brock et al. | |
| 2002/0091304 A1 | 7/2002 | Ogura et al. | |
| 2002/0138088 A1 | 9/2002 | Nash et al. | |
| 2002/0165598 A1 | 11/2002 | Wahr et al. | |
| 2002/0169377 A1 | 11/2002 | Khairkhahan et al. | |
| 2003/0130572 A1 | 7/2003 | Phan et al. | |
| 2003/0171741 A1 | 9/2003 | Ziebol et al. | |
| 2003/0208222 A1 | 11/2003 | Zadno-Azizi | |
| 2003/0212394 A1 | 11/2003 | Pearson et al. | |
| 2004/0117032 A1 | 6/2004 | Roth | |
| 2004/0158143 A1 | 8/2004 | Flaherty et al. | |
| 2004/0199052 A1 | 10/2004 | Banik et al. | |
| 2004/0210239 A1 | 10/2004 | Nash et al. | |
| 2004/0230131 A1 | 11/2004 | Kassab et al. | |
| 2004/0260182 A1 | 12/2004 | Zuluaga et al. | |
| 2005/0059954 A1 | 3/2005 | Constantz | |
| 2005/0131401 A1 | 6/2005 | Malecki et al. | |
| 2005/0159702 A1 | 7/2005 | Sekiguchi et al. | |
| 2005/0165466 A1 | 7/2005 | Morris et al. | |
| 2005/0182465 A1 | 8/2005 | Ness | |
| 2006/0025787 A1 | 2/2006 | Morales et al. | |
| 2006/0030844 A1 | 2/2006 | Knight et al. | |
| 2006/0069303 A1 | 3/2006 | Couvillon et al. | |
| 2006/0084945 A1 | 4/2006 | Moll et al. | |
| 2006/0183992 A1 | 8/2006 | Kawashima | |
| 2006/0224167 A1 | 10/2006 | Weisenburgh et al. | |
| 2006/0271032 A1 | 11/2006 | Chin et al. | |
| 2007/0106146 A1 | 5/2007 | Altmann et al. | |
| 2007/0106287 A1 | 5/2007 | O'Sullivan | |
| 2007/0167801 A1 | 7/2007 | Webler et al. | |
| 2007/0270686 A1 | 11/2007 | Ritter et al. | |
| 2008/0015569 A1 | 1/2008 | Saadat et al. | |
| 2008/0033290 A1 | 2/2008 | Saadat et al. | |
| 2008/0058590 A1 | 3/2008 | Saadat et al. | |
| 2008/0097476 A1 | 4/2008 | Peh et al. | |
| 2008/0183081 A1 | 7/2008 | Lys et al. | |
| 2008/0188759 A1 | 8/2008 | Saadat et al. | |
| 2008/0214889 A1 | 9/2008 | Saadat et al. | |
| 2008/0275300 A1 * | 11/2008 | Rothe et al. | 600/129 |
| 2008/0281293 A1 | 11/2008 | Peh et al. | |
| 2008/0287790 A1 | 11/2008 | Li | |
| 2009/0054803 A1 | 2/2009 | Saadat et al. | |
| 2009/0143640 A1 | 6/2009 | Saadat et al. | |
| 2011/0060227 A1 | 3/2011 | Saadat | |
| 2011/0060298 A1 | 3/2011 | Saadat | |
| 2011/0144576 A1 | 6/2011 | Rothe et al. | |

FOREIGN PATENT DOCUMENTS

| | | |
|---|---|---|
| EP | 0301288 A1 | 2/1999 |
| JP | 59093413 A | 5/1984 |
| JP | 59-181315 | 10/1984 |
| JP | 01-221133 | 9/1989 |
| JP | 03-284265 | 12/1991 |
| JP | 05-103746 | 4/1993 |

(56) References Cited

FOREIGN PATENT DOCUMENTS

| | | |
|---|---|---|
| JP | 09-051897 | 2/1997 |
| JP | 11-299725 | 11/1999 |
| JP | 2001-258822 | 9/2001 |
| WO | WO 92/21292 | 12/1992 |
| WO | WO 94/07413 | 4/1994 |
| WO | WO 95/03843 | 2/1995 |
| WO | WO 98/18388 | 5/1998 |
| WO | WO 03/101287 | 12/2003 |
| WO | WO 2006/083794 | 8/2006 |
| WO | WO 2008/079828 | 7/2008 |

OTHER PUBLICATIONS

U.S. Appl. No. 11/560,732, filed Nov. 16, 2006 in the name of Saadat, Notice of Allowance mailed Feb. 3, 2011.
U.S. Appl. No. 11/560,742, filed Nov. 16, 2006 in the name of Saadat, Notice of Allowance mailed Nov. 15, 2010.
U.S. Appl. No. 12/464,800, filed May 12, 2009 in the name of Peh et al., non-final Office Action mailed Nov. 24, 2010.
U.S. Appl. No. 11/848,429, filed Aug. 31, 2007 in the name of Peh et al., non-final Office Action mailed Nov. 24, 2010.
European Patent Application No. 07812146.4 filed Jun. 14, 2007 in the name of Voyage Medical, Inc., European Search Report mailed Nov. 18, 2010.
European Patent Application No. 07799466.3 filed Jul. 10, 2007 in the name of Voyage Medical, Inc., European Search Report mailed Nov. 18, 2010.
U.S. Appl. No. 12/117,655, filed May 8, 2008 in the name of Peh et al., non-final Office Action mailed Dec. 16, 2010.
U.S. Appl. No. 12/026,455, filed Feb. 5, 2008 in the name of Saadat et al., non-final Office Action mailed Dec. 27, 2010.
European Patent Application No. 06734083.6 filed Jan. 30, 2006 in the name of Saadat et al., Examination Communication mailed May 18, 2010.
European Patent Application No. 07841754.0 filed Aug. 31, 2007 in the name of Saadat et al., Supplemental European Search Report mailed Jun. 30, 2010.
European Patent Application No. 08746822.9 filed Apr. 24, 2008 in the name of Rothe et al., European Search Report mailed Mar. 29, 2010.
European Patent Application No. 08746822.9 filed Apr. 24, 2008 in the name of Rothe et al., Office Action mailed Jul. 13, 2010.
U.S. Appl. No. 11/560,742, filed Nov. 16, 2006 in the name of Saadat. Non-final Office Action mailed Jun. 10, 2010.
U.S. Appl. No. 11/687,597, filed Mar. 16, 2007 in the name of Saadat et al., Non-final Office Action mailed Jul. 21, 2010.
U.S. Appl. No. 12/117,655, filed May 8, 2008 in the name of Peh et al., Final Office Action mailed Mar. 1, 2010.
U.S. Appl. No. 61/286,283, filed Dec. 14, 2009 in the name of Rothe et al.
U.S. Appl. No. 61/297,462, filed Jan. 22, 2010 in the name of Rothe et al.
U.S. Appl. No. 11/775,771, filed Jul. 10, 2007 in the name of Saadat et al., Non-final Office Action mailed Aug. 27, 2010.
U.S. Appl. No. 11/828,267, filed Jul. 25, 2007 in the name of Saadat et al., final Office Action mailed Sep. 16, 2010.
European Patent Application No. 06734083.6 filed Jan. 30, 2006 in the name of Voyage Medical, Inc., Office Action mailed Nov. 12, 2010.
U.S. Appl. No. 12/947,198, filed Nov. 16, 2010 in the name of Saadat, non-final Office Action mailed Feb. 18, 2011.
U.S. Appl. No. 12/947,246, filed Nov. 16, 2006 in the name of Saadat, non-final Office Action mailed Feb. 18, 2011.
U.S. Appl. No. 11/687,597, filed Mar. 16, 2007 in the name of Saadat, Notice of Allowance mailed Feb. 24, 2011.
U.S. Appl. No. 11/560,732, filed Mar. 16, 2007 in the name of Saadat, Notice of Allowance mailed Feb. 24, 2011.
U.S. Appl. No. 11/848,207, filed Aug. 30, 2007 in the name of Saadat et al., non-final Office Action mailed Feb. 25, 2011.
Japanese Patent Application No. 2007-554156 filed Jan. 30, 2006 in the name of Voyage Medical, Inc., Office Action mailed Feb. 15, 2011.
European Patent Application No. 07758716.0 filed Mar. 16, 2007 in the name of Voyage Medical, Inc., Supplemental European Search Report mailed Feb. 28, 2011.
U.S. Appl. No. 11/848,202, filed Aug. 30, 2007 in the name of Saadat et al., non-final Office Action mailed Mar. 11, 2011.
U.S. Appl. No. 11/763,399, filed Jun. 14, 2007 in the name of Saadat et al., non-final Office Action mailed Apr. 11, 2011.
U.S. Appl. No. 12/499,011, filed Jul. 7, 2009 in the name of Rothe et al., non-final Office Action mailed Apr. 12, 2011.
U.S. Appl. No. 12/367,019, filed Feb. 6, 2009 in the name of Miller et al., non-final Office Action mailed Apr. 22, 2011.
U.S. Appl. No. 11/959,158, filed Dec. 18, 2007 in the name of Saadat et al., non-final Office Action mailed Apr. 25, 2011.
U.S. Appl. No. 11/848,532, filed Aug. 31, 2007 in the name of Saadat et al., non-final Office Action mailed Apr. 26, 2011.
U.S. Appl. No. 11/828,281, filed Jul. 25, 2007 in the name of Peh et al., non-final Office Action mailed Apr. 27, 2011.
U.S. Appl. No. 11/961,950, filed Dec. 20, 2007 in the name of Saadat et al., non-final Office Action mailed May 9, 2011.
U.S. Appl. No. 11/961,995, filed Dec. 20, 2007 in the name of Saadat et al., non-final Office Action mailed May 9, 2011.
U.S. Appl. No. 11/962,029, filed Dec. 20, 2007 in the name of Saadat et al., non-final Office Action mailed May 9, 2011.
U.S. Appl. No. 11/828,267, filed Jul. 25, 2007 in the name of Saadat et al., non-final Office Action mailed May 11, 2011.
Japanese Patent Application No. 2009-500630 filed Mar. 16, 2007 in the name of Voyage Medical, Inc., Office Action mailed Apr. 27, 2011.
U.S. Appl. No. 11/775,771, filed Jul. 10, 2007 in the name of Saadat et al., final Office Action mailed May 12, 2011.
U.S. Appl. No. 11/877,386, filed Oct. 23, 2007 in the name of Saadat et al., non-final Office Action mailed May 20, 2011.
U.S. Appl. No. 11/775,819, filed Jul. 10, 2007 in the name of Saadat et al., non-final Office Action mailed May 20, 2011.
U.S. Appl. No. 11/775,837, filed Jul. 10, 2007 in the name of Saadat et al., non-final Office Action mailed May 23, 2011.
U.S. Appl. No. 12/117,655, filed May 8, 2008 in the name of Peh et al., final Office Action mailed Jun. 2, 2011.
U.S. Appl. No. 12/323,281, filed Nov. 25, 2008 in the name of Saadat et al., non-final Office Action mailed Jun. 7, 2011.
Japanese Patent Application No. 2007-554156 filed Jan. 30, 2006 in the name of Voyage Medical, Inc., Notice of Allowance mailed Jun. 13, 2011.

\* cited by examiner

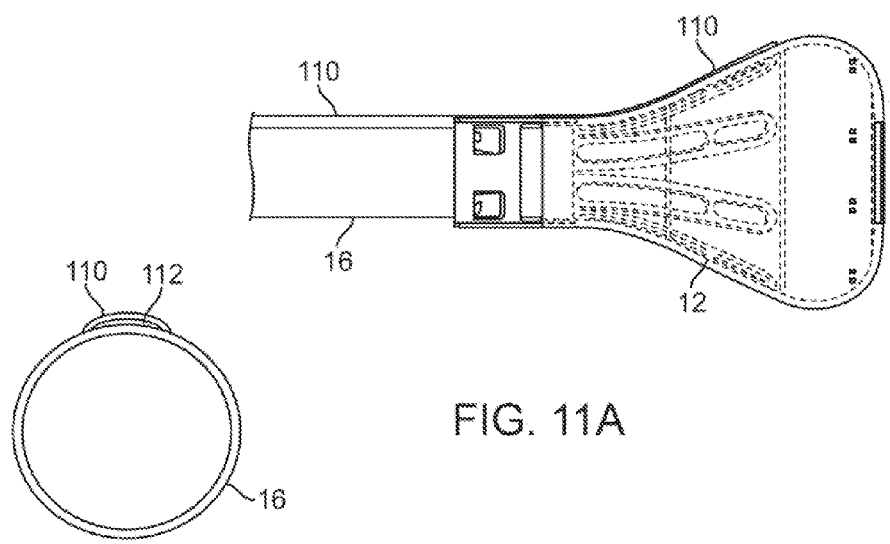
FIG. 11A
FIG. 11B
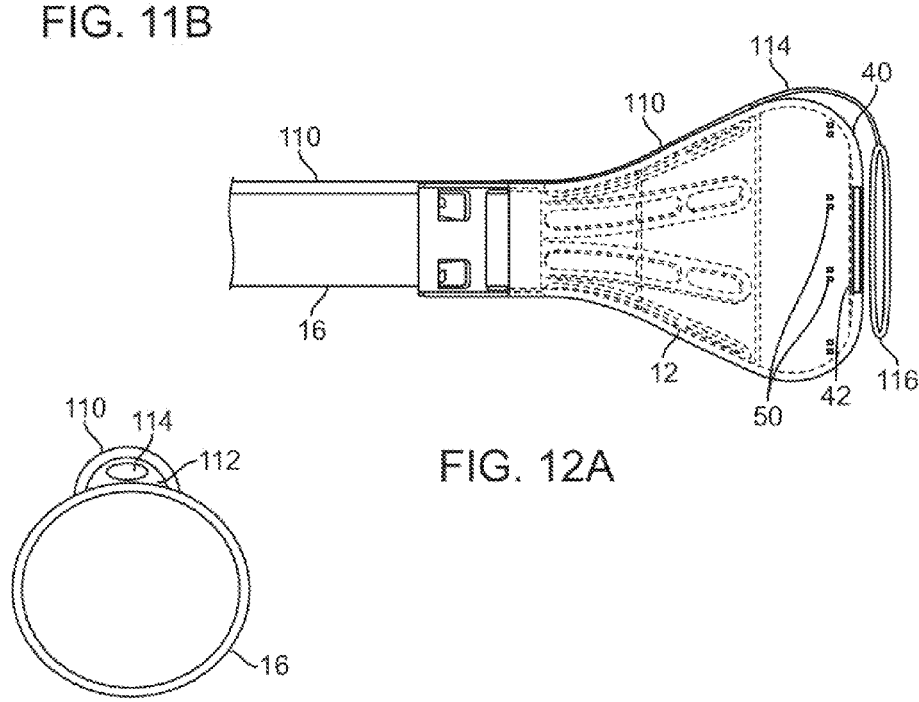
FIG. 12A
FIG. 12B

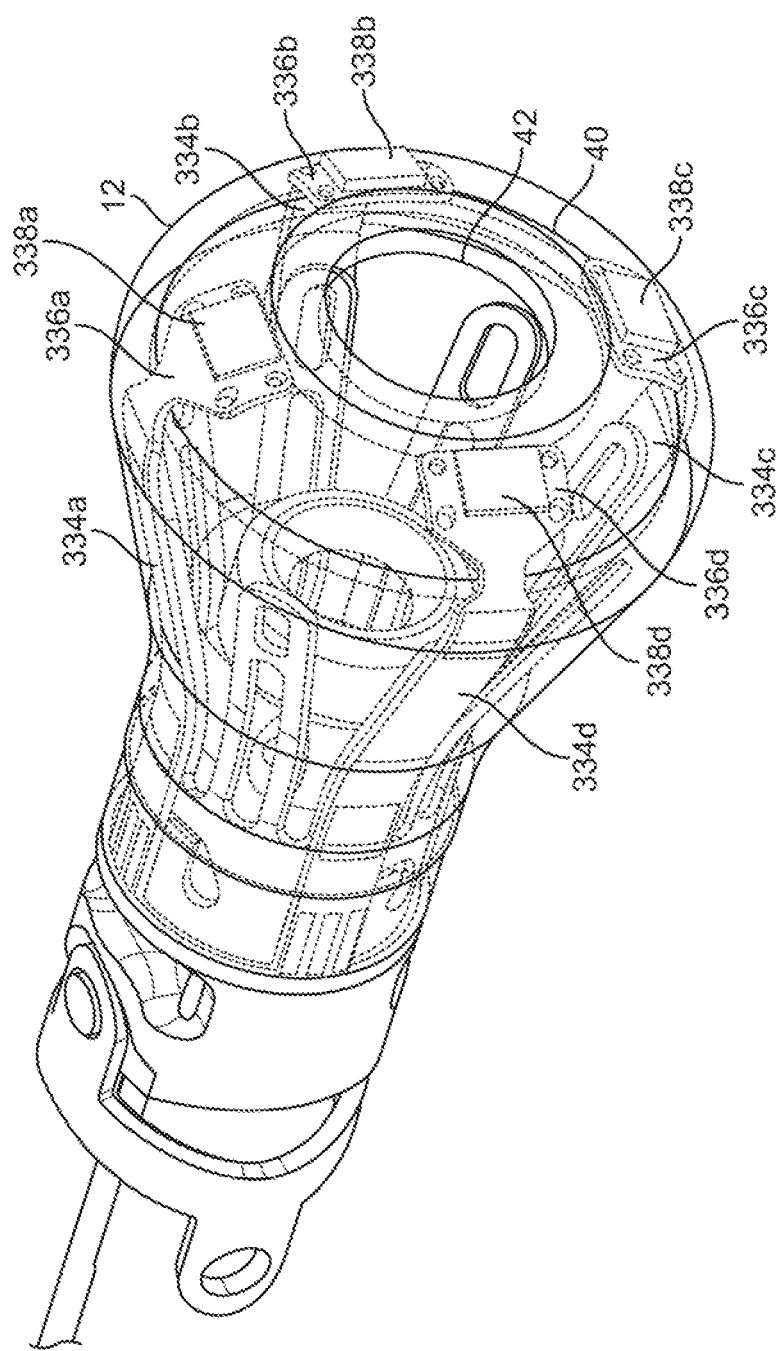

INTEGRAL ELECTRODE PLACEMENT AND CONNECTION SYSTEMS

CROSS-REFERENCE TO RELATED APPLICATIONS

This application claims the benefit of priority to U.S. Prov. Pat App. 61/177,619 filed May 12, 2009 and is also a continuation-in-part of U.S. patent application Ser. No. 12/575,674 filed Oct. 8, 2009, which claims the benefit of priority to U.S. Prov. Pat. App. 61/104,650 filed Oct. 10, 2008, each of which is incorporated herein by reference in its entirety.

FIELD OF THE INVENTION

The present invention relates generally to medical devices used for accessing, visualizing, and/or treating regions of tissue within a body. More particularly, the present invention relates to methods and apparatus for visualizing and/or treating regions of tissue within a body, such as the chambers of a heart, while electrically connecting to and maintaining connections to one or more electrodes positioned on the device which is subjected to a variety of mechanical stresses.

BACKGROUND OF THE INVENTION

Conventional devices for accessing and visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult.

Other external imaging modalities are also conventionally utilized. For example, computed tomography (CT) and magnetic resonance imaging (MRI) are typical modalities which are widely used to obtain images of body lumens such as the interior chambers of the heart. However, such imaging modalities fail to provide real-time imaging for intra-operative therapeutic procedures. Fluoroscopic imaging, for instance, is widely used to identify anatomic landmarks within the heart and other regions of the body. However, fluoroscopy fails to provide an accurate image of the tissue quality or surface and also fails to provide for instrumentation for performing tissue manipulation or other therapeutic procedures upon the visualized tissue regions. In addition, fluoroscopy provides a shadow of the intervening tissue onto a plate or sensor when it may be desirable to view the intraluminal surface of the tissue to diagnose pathologies or to perform some form of therapy on it.

Moreover, many of the conventional imaging systems lack the capability to provide therapeutic treatments or are difficult to manipulate in providing effective therapies. For instance, the treatment in a patient's heart for atrial fibrillation is generally made difficult by a number of factors, such as visualization of the target tissue, access to the target tissue, and instrument articulation and management, amongst others.

Additionally, treating such tissue regions is further complicated by limitations in the instruments. Delivering a treatment instrument intravascularly typically requires that the instrument maintain a low delivery profile so as to prevent trauma to surrounding tissues. However, once reaching the target location, the instrument may reconfigure itself into a larger profile, particularly when used to provide visualization of the area to be treated. Yet treatment modalities such as the application of energy, e.g., radio frequency energy, through one or more electrodes which may be positioned along the instrument need to remain reliably in electrical communication with a power supply and/or processor which is typically located outside the patient body.

Thus, a tissue imaging system which is able to provide real-time in vivo access to and images of tissue regions and which also maintains reliable electrical communication for treating such tissue regions through instrument reconfigurations is desired.

SUMMARY OF THE INVENTION

Reconfiguring a tissue visualization and treatment device from a low profile delivery configuration for intravascular delivery through the vessels of a patient to a deployed and expanded configuration may subject the distal end effector used for visualization and/or treatment, such as energy delivery, to potentially severe mechanical stresses (e.g., torsion, compression, tension, shearing, etc.). For example, a reconfigurable hood which undergoes a shape change from its collapsed configuration to an expanded conical shape may utilize a distensible, collapsible, and/or reconfigurable substrate which may utilize electrode placement and electrical connection assemblies which are robust and able to withstand such stresses.

In describing the tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or assembly may be disposed for imaging tissue. When deployed, the imaging hood may be expanded into any number of shapes, e.g., cylindrical, conical as shown, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control.

The deployment catheter may also be stabilized relative to the tissue surface through various methods. For instance, inflatable stabilizing balloons positioned along a length of the catheter may be utilized, or tissue engagement anchors may be passed through or along the deployment catheter for temporary engagement of the underlying tissue.

In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

In an exemplary variation for imaging tissue surfaces within a heart chamber containing blood, the tissue imaging and treatment system may generally comprise a catheter body having a lumen defined therethrough, a visualization element disposed adjacent the catheter body, the visualization element having a field of view, a transparent fluid source in fluid communication with the lumen, and a barrier or membrane extendable from the catheter body to localize, between the visualization element and the field of view, displacement of blood by transparent fluid that flows from the lumen, and an instrument translatable through the displaced blood for performing any number of treatments upon the tissue surface within the field of view. The imaging hood may be formed into any number of configurations and the imaging assembly may also be utilized with any number of therapeutic tools which may be deployed through the deployment catheter.

More particularly in certain variations, the tissue visualization system may comprise components including the imaging hood, where the hood may further include a membrane having a main aperture and additional optional openings disposed over the distal end of the hood. An introducer sheath or the deployment catheter upon which the imaging hood is disposed may further comprise a steerable segment made of multiple adjacent links which are pivotably connected to one another and which may be articulated within a single plane or multiple planes. The deployment catheter itself may be comprised of a multiple lumen extrusion, such as a four-lumen catheter extrusion, which is reinforced with braided stainless steel fibers to provide structural support. The proximal end of the catheter may be coupled to a handle for manipulation and articulation of the system.

To provide visualization, an imaging element such as a fiberscope or electronic imager such as a solid state camera, e.g., CCD or CMOS, may be mounted, e.g., on a shape memory wire, and positioned within or along the hood interior. A fluid reservoir and/or pump (e.g., syringe, pressurized intravenous bag, etc.) may be fluidly coupled to the proximal end of the catheter to hold the translucent fluid such as saline or contrast medium as well as for providing the pressure to inject the fluid into the imaging hood.

In clearing the hood of blood and/or other bodily fluids, it is generally desirable to purge the hood in an efficient manner by minimizing the amount of clearing fluid, such as saline, introduced into the hood and thus into the body. As excessive saline delivered into the blood stream of patients with poor ventricular function may increase the risk of heart failure and pulmonary edema, minimizing or controlling the amount of saline discharged during various therapies, such as atrial fibrillation ablation, atrial flutter ablation, transseptal puncture, etc. may be generally desirable.

Turning now to the electrode assemblies and connection systems utilized with the collapsible hood, these electrodes (e.g., electrode pairs) may be used to deliver electrical energy such as radio-frequency energy to tissue in direct contact with or in proximity to the electrodes to form lesions upon the tissue surface as well as underlying tissue regions. Additionally, the electrodes or electrode pairs may be positioned about the hood in a uniform or non-uniform manner depending upon the desired configuration. Moreover, these electrodes may also be used to deliver energy into and/or through the purging fluid which may contact the electrodes for conducting the energy through the fluid and into the underlying tissue region being treated. Alternatively, one or more of these electrodes may also be used to detect and/or measure any electrophysiological activity of the contacted tissue prior to, during, or after tissue treatment.

One example is a hood where one or more electrodes or electrode pairs may be positioned (uniformly or non-uniformly) about the main aperture. The electrodes may thus contact the underlying tissue when placed into apposition against the tissue region to be visualized and/or treated or they may conduct the energy through the purging fluid into the tissue as the fluid passes over the electrodes from the hood interior. Each of the electrodes may be formed or adhered directly to the hood surface or they may also be integrated directly into the hood material. In either case, each of the electrodes may be connected via an electrical connection (e.g., metal wires, filament strand material, conductive polymers, silver emulsion, carbon black track, carbon nanotubes, graphite fiber, metal film deposition or conductive fluids, etc.) to a proximal end of the hood and through the catheter to power supply and/or signal processor. Alternatively, the one or more electrodes may be positioned upon the distal membrane circumferentially about the main aperture, circumferentially about the hood proximally of the distal curved portion, circumferentially about the hood distal to the hood connecting member, or even longitudinally between the main aperture and connecting member.

The electrodes may be secured or adhered directly to the outer surface of the hood as pads or contacts or elsewhere along the hood. The one or more electrodes may be formed into various shapes, e.g., square, rectangular, circular, triangular, etc. or other alternative shapes such as an I-shape where the electrodes extend between the outer surface and the inner surface of the hood membrane. Another variation may comprise spherically-shaped electrodes integrated along the hood such that a portion of the electrodes is embedded within the hood while a remainder projects distally from the hood outer surface. Yet another variation may include conically-shaped electrodes where the base portion of each electrode may be embedded within the hood material while the apex of the electrode extends past the outer surface of the hood and projects distally for contact against or into proximity with the tissue to be treated. In this and the other variations, the electrodes are positioned upon or within the hood such that they are securely attached thereto. Thus, while the hood is collapsed and/or expanded, the one or more electrodes may remain securely adhered or attached to the hood.

Another variation may include one or more electrodes which are shaped as elongate elements which extend radially from the main aperture over the distal membrane. Each of the electrodes may extend over the distal membrane and project distally from the surface of membrane. In yet other variations, one or more electrodes may be positioned upon expandable chambers defined along the hood outer surface while another variation comprises a distensible, flexible, and/or scaffold-like material which may be placed directly over the hood assembly. The covering assembly may be comprised of a mesh-like or elastic material or the same or similar material as the hood and have one or more electrodes positioned upon a contact portion of the covering which may slide upon the distal membrane of the hood.

Another variation may comprise an expandable delivery channel formed along the length of the catheter and extending at least partially along the hood such that a lumen is defined through the length of the channel. An electrode assembly, for example, a reconfigurable ring electrode advanced upon an electrode shaft, may be advanced through the length of the expandable channel in a low profile and deployed distal to the hood once the hood has been desirably expanded.

Another example is a hood assembly having one or more extended struts which extend from the catheter to the distal end of the hood. The one or more extended struts may extend past the remaining struts such that the distal ends of the extended struts are flush with or project past the distal membrane to contact the underlying tissue. The extended struts may thus have electrodes positioned upon their distal ends for placement against the tissue while maintaining an electrical connection through the struts. Utilizing the struts as electrodes may take advantage of the robustness and strength provided by the struts which are better suited to handle the mechanical stresses imparted upon the electrodes during hood delivery and deployment.

Another variation includes the hood assembly configured to collapse or fold in a predetermined and consistent manner such that electrodes may be placed at locations upon the hood which have a lower stress potential, e.g., along a portion of the hood which is not folded for delivery or collapse. One mechanism for achieving this is to utilize struts of different lengths. For instance, struts which extend along the hood may be alternated with shortened struts which are relatively shorter in length. Because of the additional space created by the shortened struts when the hood is collapsed, the collapsed portions of the hood may collapse or fold consistently between the struts along where the shortened struts fold. Accordingly, with the hood collapsing in a consistent folding pattern, electrodes or wires may be positioned along portions of the hood which are not folded aside from the collapsed portions.

In yet another variation, the maintenance of the hood in its collapsed configuration allows for the initial retraction within the sheath and subsequent deployment from the sheath with a reduced stress load on the hood as friction and sliding contact between the hood and sheath is reduced. A restraining member may comprise a wire or ribbon which may be wrapped about the struts of the hood to restrain the hood from expansion. Once the hood is ready to be deployed and/or expanded, the hood may be advanced from the sheath and a tensioning member or release may be pulled or actuated to release the restraining member from around the hood by releasing a knot or simply breaking the restraining member. Another example is a hood having a bi-stable strut assembly, i.e., struts which are preformed to have at least two mechanically stable configurations. When advanced distally for deployment or actuated via a mechanism (such as a push/pull wire), the hood may transition from its stable low-profile configuration into a second configuration which is also mechanically stable.

In maintaining electrical communication with the one or more electrodes positioned at various locations upon the hood, electrical traces may be laid upon the hood for maintaining electrical communication with the various electrodes. Such traces may be made of conductive materials through any number of methods, e.g., chemical vapor deposition, laser etching, micropen writing, adhesives, etc. Moreover, in laying down the traces upon or within the hood, the traces are desirably insulated along their lengths through any number of mechanisms. Additionally, use of traces placed within or along the hood allows for added flexibility in connecting the electrodes along the hood to a power source and/or processor.

By integrating the conductive traces within the hood itself, a robust electrical connection to the one or more electrodes may be maintained as the hood reconfigures between its low profile and deployed shapes. A mandrel shaped in the form of the hood in its deployed configuration may be coated first with a first layer such as an elastomeric material (e.g., silicone, chronoflex, polyurethane, etc.) which may be sufficiently dried or cured. The mandrel may also optionally define one or more grooves or channels within which the traces may be laid to form a smooth exterior surface. One or more conductive traces may be then laid upon the first layer utilizing any of the methods mentioned and in any number of desired patterns extending along or over the first layer and proximally along the mandrel for electrical connection. With the conductive traces sufficiently cured, a second layer of material which may be the same or a similar material as the first layer may then be laid atop both the first layer and the conductive traces to sandwich and electrical insulate the conductive traces from the environment as well as from one another. With the second layer of material cured or dried, the mandrel may then be removed either physically or chemically from the conductive hood assembly.

In one variation, with a mandrel made of a material such as acrylic, the mandrel may provide the desired structural support for building the layers of material and conductive traces and when the mandrel is to be removed, the entire assembly may be soaked in a chemical such as acetone to dissolve the mandrel yet leave the first and second layers and sandwiched conductive traces intact. With the mandrel removed, the remaining hood structure may have one or more apertures, such as a main aperture, formed or cut into the distal membrane portion of the hood. Moreover, one or more electrodes may also be positioned anywhere along the length of the conductive traces by exposing a corresponding portion of the underlying sandwiched trace.

In yet another variation for forming conductive traces along the exterior or interior surface of the hood, a flexible electrode assembly formed of one or more conductive traces which are encased or integrated within a polymeric substrate may be formed in a similar process. The assembly may be formed into a conical structure which may then be laid atop a mandrel for subsequent coating by additional layers of elastomeric material. This particular variation may facilitate the manufacturability of the hood having integrated conductive traces within. The hood can also be formed with electrodes in a single layer through a process called insert molding. The flex circuit ay be held in or near the center of the silicone wall by projections from the cavity and core of the injection mold tool and silicone or other elastomer may be molded around the flex circuit or electrode assembly. The projections leave holes in the elastomer which will be closed or alternately, the projections could contact the flex circuit on its exterior side where there are electrodes and/or on its interior surface by contacting on non-conductive portions of the flex circuit. In yet another variation, the flex circuit may have silicone projections molded onto it at selected locations in a first operation. The silicone projections may then hold the flex circuit when it is loaded into a mold tool in or near a center of the injection mold tool (e.g., between the mandrel and the cavity of the tool) so that silicone can be molded around it.

Turning now to the trace connections which connect the electrodes to the power supply and/or signal processer (or any other unit), such traces are desirably robust enough to withstand the high mechanical stresses which are imparted to the traces as the hood undergoes introduction and removal from the sheath as well as the reconfiguration between its low profile and deployed profile. As such, the traces may be laid in any number of patterns which may alleviate the stresses imparted to the traces. Traces may accordingly be laid in, e.g., straight, curved, saw-tooth, or even looped and/or helical patterns.

Aside from use of conductive traces, alternative mechanisms for maintaining robust electrical communication to electrodes positioned on a deployable hood may utilize conducting wires which are structurally robust enough to endure the stresses imparted on them. One example is a conductive cable assembly positioned to extend along the length of the hood or in a helical pattern about the hood to form a looped portion at least partially encircling the main aperture. The looped portion may comprise one or more exposed electrode segments for contact against the underlying tissue. In forming a mechanically and electrically robust cable assembly, the cable may generally comprise a core wire having a first diameter which provides mechanical strength to the assembly. The core wire may be surrounded by individual lengths of adjacent conductive wires each of which have a second diameter which is smaller than the first diameter of the core wire. The entire assembly may be encased by an insulative outer covering which may be exposed at regions where the electrode segments are positioned.

Another variation for forming a robust system for maintaining electrical communication may include an expandable electrode assembly separate from the hood. The electrode assembly may generally comprise a conductive support member having one or more conductive branching members which are reconfigurable from a low profile configuration, where each of the branching members are compressed, to an expanded configuration, where several branching members may reconfigure into a deployed configuration. Each of the deployed branching members may extend at an angle such that the members come into electrical contact with corresponding electrode pads positioned along the hood. By separating the hood from the electrical conductor assembly, the connection system is not subjected to the mechanical stresses normally imparted by the reconfiguring hood.

In addition to the electrical connections to the electrodes positioned on the hood, termination of the connection systems from the hood assembly and to or through the delivery catheter is also a consideration as electrical isolation, robustness, ease of manufacturability, etc. are of concern as well. One such variation of a hood assembly having a connector base may include one or more electrode connector pins projecting from the connector base. The one or more connector pins may be electrically coupled to one or more corresponding electrodes positioned within or along the hood. The hood assembly may be connected, electrically as well as mechanically, to the catheter by the insertion of connector pins into one or more electrode receiving slots which may be in electrical communication with a power supply and/or processor through the length of the catheter. The insertion and coupling of the connector pins with the receiving slots helps to ensure a secure electrical and mechanical connection as the hood is delivered and deployed.

In yet another variation, a hood assembly having a connector base with one or more conductive studs or projections extending from the base may be configured to be locked into the catheter distal end. Because the studs or projections extend from a surface of the base, a receiving channel may be defined longitudinally along the distal end of the catheter. The receiving channel may further define a locking channel which extends from receiving channel at an angle, e.g., perpendicularly, such that as the base of the hood assembly is coupled to the catheter the base is forced to be twisted as the one or more projections are guided along receiving channel and then along the angled locking channel. Moreover, the twisting of the hood assembly relative to the catheter further helps to ensure rigidity of the coupling as well as electrical isolation between electrodes.

In yet another example, rather than having conductive wires transmit signals to and from the one or more electrodes within or along the hood and to a power supply or processor located separately from the catheter assembly, the electrical connection systems to and from the electrodes may be terminated locally along the hood assembly itself. The electrodes may be electrically coupled to a local signal processor attached, e.g., to the base of the hood assembly. The signal processor may generally comprise at least a single microprocessor for processing and outputting any received and processed signal through a single wire passed through the catheter. Such a design may facilitate the electrical connection to the electrodes as well as facilitate the manufacturability of the hood assembly by reducing the number of connecting wires.

Any of the electrode assemblies show and described herein may be utilized for various purposes aside for the delivery of ablation energy. For example, the electrode assemblies may be utilized for detecting or sensing electrical energy transmitted through the underlying tissue of interest. Such electrodes may be used to detect or sense the electrical energy naturally conducted through the body for electrocardiogram measurements, cardiac pacing, etc., prior to tissue treatment for electro-anatomical mapping. Alternatively, these signals may be detected during a tissue treatment or after for determining the efficacy of a treatment, e.g., ablation energy delivered into the tissue for creating a conduction block.

The structure of the circuit assembly for forming and/or connecting the electrodes along the hood structure can generally be one of two types. In a first example, most or all of the electrodes may be formed on a single circuit element while in a second example, most or all of the electrodes may be formed onto multiple circuit elements. In this latter form, the multiple elements may be configured in the same manner, but may be of a limited number of types; for instance, one type of element may be used for detecting or sensing electro-anatomical mapping while another type may be used for detecting or sensing electrocardiograms.

The use of wafer, roll, or sheet scale manufacturing for producing electrical circuit traces may be used to form large quantities of flat, flexible circuits that may be incorporated in the hood. Electrical traces may be laid upon sheets or rolls of a flexible polymeric base layer such as polyimide or polyester, etc., via processes used in the fabrication of printed circuit boards. The polymer base layer and its traces may then be covered in at least a second sheet of a polymer overcoat layer and the circuit assembly may be further processed, as desired or necessary, to configure the circuit assembly into a configuration for integration along the hood.

Portions of the circuit assembly may extend upon the distal membrane of the hood into proximity with the aperture and may serve a dual function. For instance, the distal circuit portion may have one or more exposed electrodes which may be placed into direct contact against the tissue surface, e.g., for detecting electrical activity of the tissue. Additionally, the distal circuit portion may also serve to provide structural support to the aperture such that distortion of the aperture is prevented by the presence of the circuit portions when contacted against the tissue for detection and/or for tissue treatment such as during ablation energy delivery through the aperture.

BRIEF DESCRIPTION OF THE DRAWINGS

FIGS. 11A and 11B show side and cross-sectional end views, respectively, of a variation which utilizes a flexible and/or distensible material to form a channel extending along the catheter and hood through which an electrode assembly may be advanced.

FIGS. 12A and 12B show side and cross-sectional end views, respectively, of the device of FIGS. 11A and 11B with an electrode assembly advanced through the channel and extended past the hood.

FIG. 29C shows a perspective view of another variation of the electrode array assembly having four electrodes extending along the hood and positioned uniformly in a radial manner about the aperture.

DETAILED DESCRIPTION OF THE INVENTION

Reconfiguring a tissue visualization and treatment device from a low profile delivery configuration for intravascular delivery through the vessels of a patient to a deployed and expanded configuration may subject the distal end effector used for visualization and/or treatment, such as energy delivery, to potentially severe mechanical stresses (e.g., torsion, compression, tension, shearing, etc.). For example, a reconfigurable hood which undergoes a shape change from its collapsed configuration to an expanded conical shape may utilize a distensible, collapsible, and/or reconfigurable substrate which may utilize electrode placement and electrical connection assemblies which are robust and able to withstand such stresses. Such electrical connection assemblies may be shielded or insulated from contacting other structures so as to present a smooth or unobstructive profile for reconfiguring with the hood.

Turning now to the tissue-imaging and manipulation apparatus upon which one or more electrodes may be positioned and which is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures.

Figure 1A:
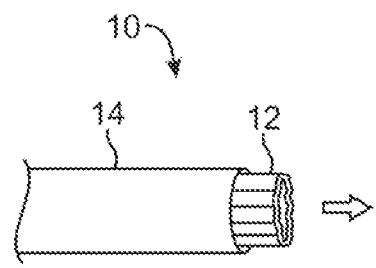
FIG. 1A shows a side view of one variation of a tissue imaging apparatus during deployment from a sheath or delivery catheter.
Figure 1B:
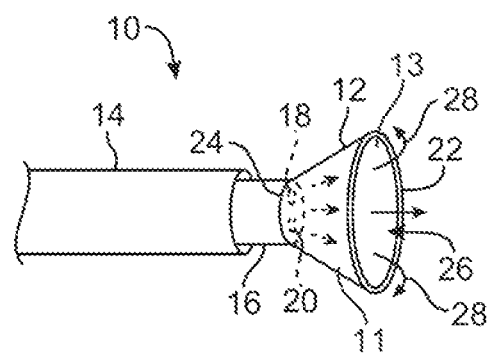
FIG. 1B shows the deployed tissue imaging apparatus of FIG. 1A having an optionally expandable hood or sheath attached to an imaging and/or diagnostic catheter.
Figure 1C:
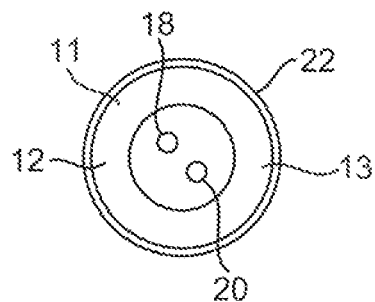
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, it is generally desirable to enter or access the left atrium while minimizing trauma to the patient. To non-operatively effect such access, one conventional approach involves puncturing the intraatrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 2A:
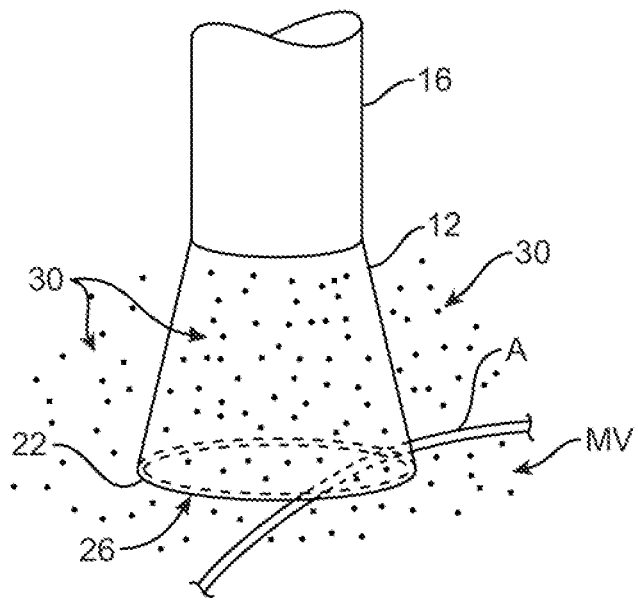
FIGS. 2A and 2B show one example of a deployed tissue imager positioned against or adjacent to the tissue to be imaged and a flow of fluid, such as saline, displacing blood from within the expandable hood.
Figure 2B:
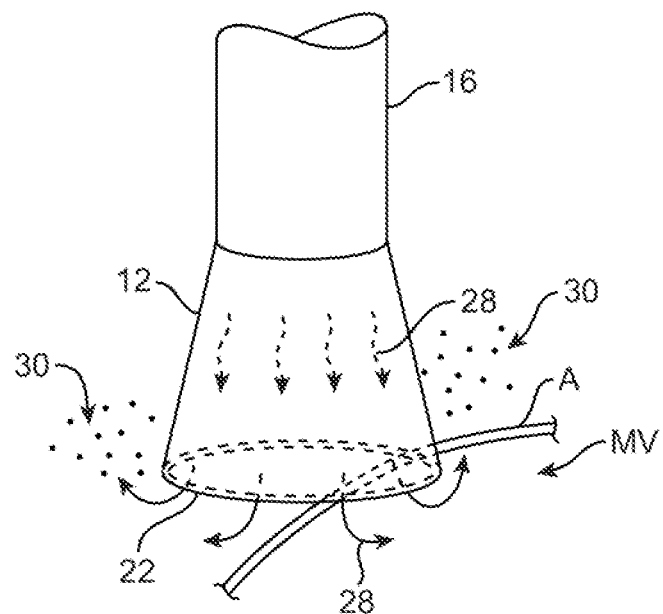

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant back-flow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
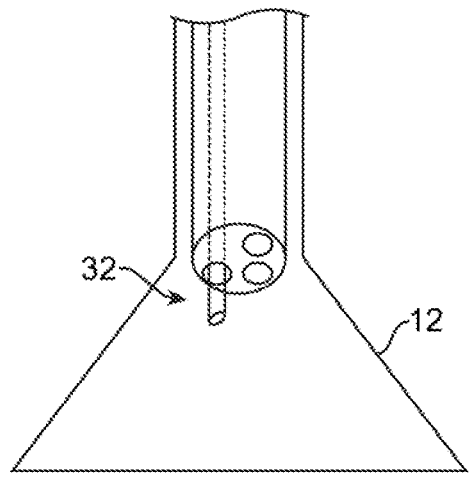
FIGS. 3A and 3B show examples of various visualization imagers which may be utilized within or along the imaging hood.
Figure 3B:
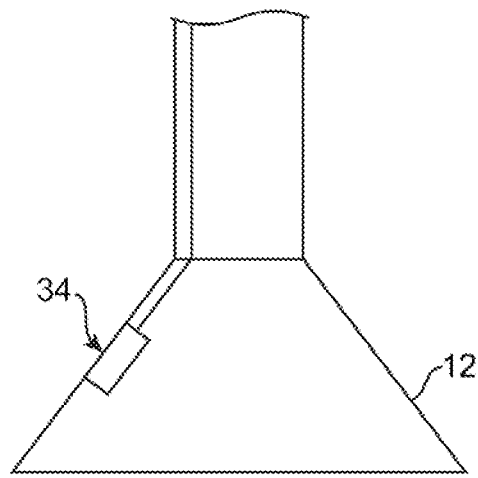

FIG. 3A shows a partial cross-sectional view of an example where one or more optical fiber bundles 32 may be positioned within the catheter and within imaging hood 12 to provide direct in-line imaging of the open area within hood 12. FIG. 3B shows another example where an imaging element 34 (e.g., CCD or CMOS electronic imager) may be placed along an interior surface of imaging hood 12 to provide imaging of the open area such that the imaging element 34 is off-axis relative to a longitudinal axis of the hood 12, as described in further detail below. The off-axis position of element 34 may provide for direct visualization and uninhibited access by instruments from the catheter to the underlying tissue during treatment.

Figure 4A:
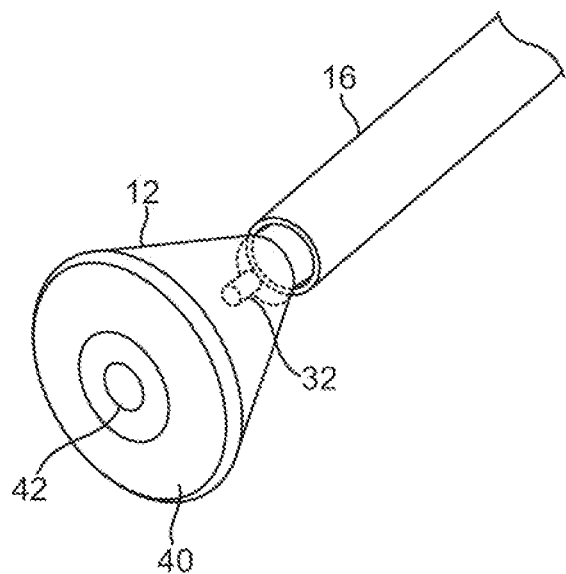
FIGS. 4A and 4B show perspective and end views, respectively, of an imaging hood having at least one layer of a transparent elastomeric membrane over the distal opening of the hood.
Figure 4B:
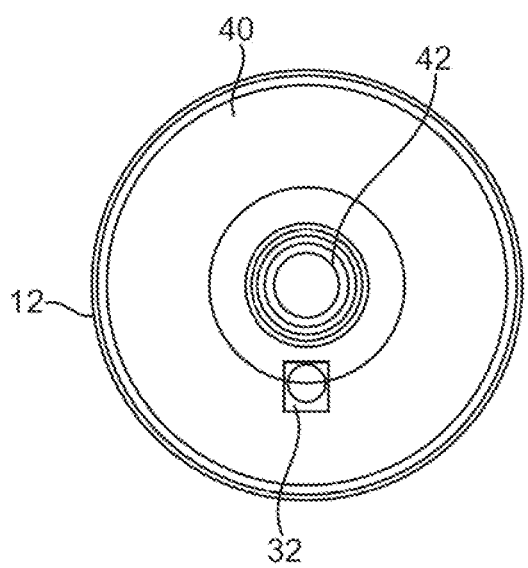

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations. An additional variation of the imaging hood 12 is shown in the perspective and end views, respectively, of FIGS. 4A and 4B, where imaging hood 12 includes at least one layer of a transparent elastomeric membrane 40 over the distal opening of hood 12. An aperture 42 having a diameter which is less than a diameter of the outer lip of imaging hood 12 may be defined over the center of membrane 40 where a longitudinal axis of the hood intersects the membrane such that the interior of hood 12 remains open and in fluid communication with the environment external to hood 12. Furthermore, aperture 42 may be sized, e.g., between 1 to 2 mm or more in diameter and membrane 40 can be made from any number of transparent elastomers such as silicone, polyurethane, latex, etc. such that contacted tissue may also be visualized through membrane 40 as well as through aperture 42.

Aperture 42 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 42 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 42 may be aligned with catheter 16 such that any instruments (e.g., piercing instruments, guidewires, tissue engagers, etc.) that are advanced into the hood interior may directly access the underlying tissue uninhibited or unrestricted for treatment through aperture 42. In other variations wherein aperture 42 may not be aligned with catheter 16, instruments passed through catheter 16 may still access the underlying tissue by simply piercing through membrane 40.

Figure 5A:
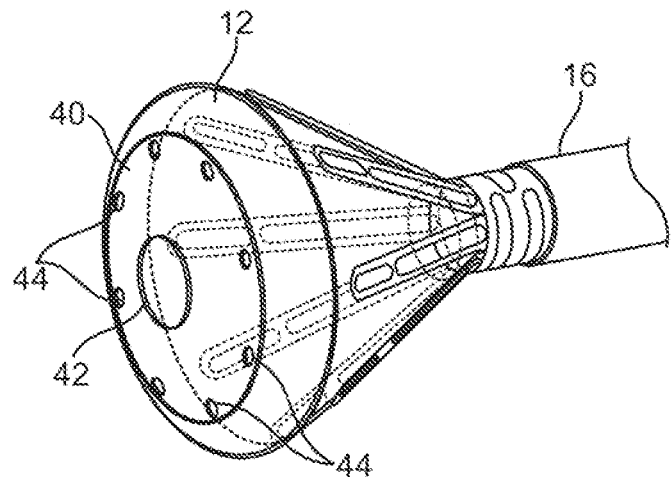
FIGS. 5A and 5B show perspective and end views, respectively, of an imaging hood which includes a membrane with an aperture defined therethrough and a plurality of additional openings defined over the membrane surrounding the aperture.
Figure 5B:
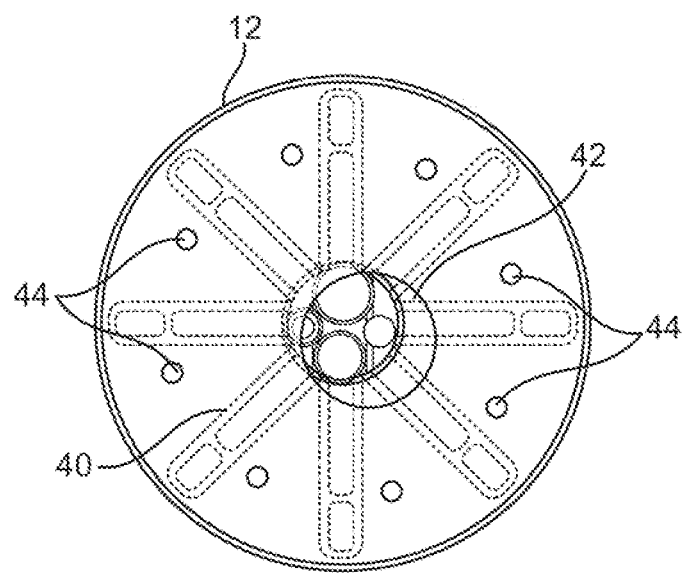

In an additional variation, FIGS. 5A and 5B show perspective and end views, respectively, of imaging hood 12 which includes membrane 40 with aperture 42 defined therethrough, as described above. This variation includes a plurality of additional openings 44 defined over membrane 40 surrounding aperture 42. Additional openings 44 may be uniformly sized, e.g., each less than 1 mm in diameter, to allow for the out-flow of the translucent fluid therethrough when in contact against the tissue surface. Moreover, although openings 44 are illustrated as uniform in size, the openings may be varied in size and their placement may also be non-uniform or random over membrane 40 rather than uniformly positioned about aperture 42 in FIG. 5B. Furthermore, there are eight openings 44 shown in the figures although fewer than eight or more than eight openings 44 may also be utilized over membrane 40.

Additional details of tissue imaging and manipulation systems and methods which may be utilized with apparatus and methods described herein are further described, for example, in U.S. patent application Ser. No. 11/259,498 filed Oct. 25, 2005 (U.S. Pat. Pub. 2006/0184048 A1), which is incorporated herein by reference in its entirety.

In utilizing the devices and methods above, various procedures may be accomplished. One example of such a procedure is crossing a tissue region such as in a transseptal procedure where a septal wall is pierced and traversed, e.g., crossing from a right atrial chamber to a left atrial chamber in a heart of a subject. Generally, in piercing and traversing a septal wall, the visualization and treatment devices described herein may be utilized for visualizing the tissue region to be pierced as well as monitoring the piercing and access through the tissue. Details of transseptal visualization catheters and methods for transseptal access which may be utilized with the apparatus and methods described herein are described in U.S. patent application Ser. No. 11/763,399 filed Jun. 14, 2007 (U.S. Pat. Pub. 2007/0293724 A1), which is incorporated herein by reference in its entirety. Additionally, details of tissue visualization and manipulation catheter which may be utilized with apparatus and methods described herein are described in U.S. patent application Ser. No. 11/259,498 filed Oct. 25, 2005 (U.S. Pat. Pub. 2006/0184048 A1), which is incorporated herein by reference in its entirety.

In clearing the hood of blood and/or other bodily fluids, it is generally desirable to purge the hood in an efficient manner by minimizing the amount of clearing fluid, such as saline, introduced into the hood and thus into the body. As excessive saline delivered into the blood stream of patients with poor ventricular function may increase the risk of heart failure and pulmonary edema, minimizing or controlling the amount of saline discharged during various therapies, such as atrial fibrillation ablation, atrial flutter ablation, transseptal puncture, etc. may be generally desirable.

Turning now to the electrode assemblies and connection systems utilized with the collapsible hood, various examples are described herein which illustrate variations for electrode positioning along the hood which may minimize or reduce the degree of stress imparted to the electrode assemblies. These electrodes (e.g., electrode pairs) may be used to deliver electrical energy such as radio-frequency energy to tissue in direct contact with or in proximity to the electrodes to form lesions upon the tissue surface as well as underlying tissue regions. Additionally, the electrodes or electrode pairs may be positioned about the hood in a uniform or non-uniform manner depending upon the desired configuration. Moreover, these electrodes may also be used to deliver energy into and/or through the purging fluid which may contact the electrodes for conducting the energy through the fluid and into the underlying tissue region being treated. Alternatively, one or more of these electrodes may also be used to detect and/or measure any electrophysiological activity of the contacted tissue prior to, during, or after tissue treatment.

While specific examples of the visualization and treatment hood are shown herein, other variations and examples of hoods and tissue treatment systems may be utilized with the devices and methods described herein. For example, the hoods, systems, and other features as described in Ser. No. 11/259,498 filed Oct. 25, 2005 (U.S. Pat. Pub. 2006/0184048 A1); Ser. No. 11/775,837 filed Jul. 10, 2007 (U.S. Pat. Pub. 2008/0009747, A1); Ser. No. 12/118,439 filed May 9, 2008 (U.S. Pat. Pub. 2009/0030412 A1); Ser. No. 12/201,811 filed Aug. 29, 2008 (U.S. Pat. Pub. 2009/0062790 A1); and Ser. No. 12/209,057 filed Sep. 11, 2008 (U.S. Pat. Pub. 2009/0076498 A1), may be utilized herewith. Each of these applications is incorporated herein by reference in its entirety.

Figure 6A:
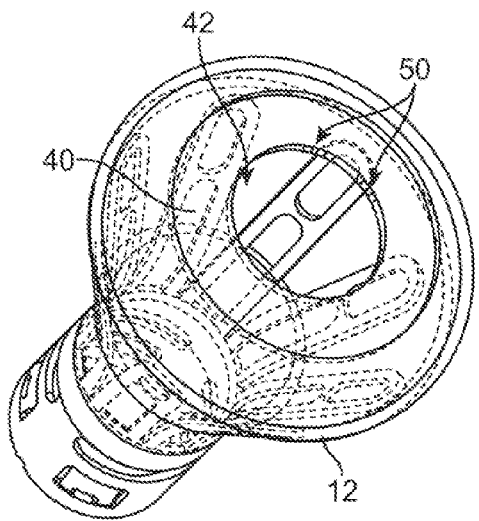
FIG. 6A shows a perspective view of one variation where one or more electrodes may be positioned about an opening of the main aperture.

FIG. 6A illustrates one example of a hood shown in a perspective view where one or more electrodes or electrode pairs 50 may be positioned (uniformly or non-uniformly) about the main aperture 42. The electrodes 50 may thus contact the underlying tissue when placed into apposition against the tissue region to be visualized and/or treated or they may conduct the energy through the purging fluid into the tissue as the fluid passes over the electrodes from the hood interior. Each of the electrodes 50 may be formed or adhered directly to the hood surface or they may also be integrated directly into the hood material (as described in further detail below). In either case, each of the electrodes 50 may be connected via an electrical connection (e.g., metal wires, filament strand material, conductive polymers, silver emulsion, carbon black track, carbon nanotubes, graphite fiber, metal film deposition or conductive fluids, etc.) to a proximal end of the hood 12 and through the catheter to power supply and/or signal processor.

Figure 6B:
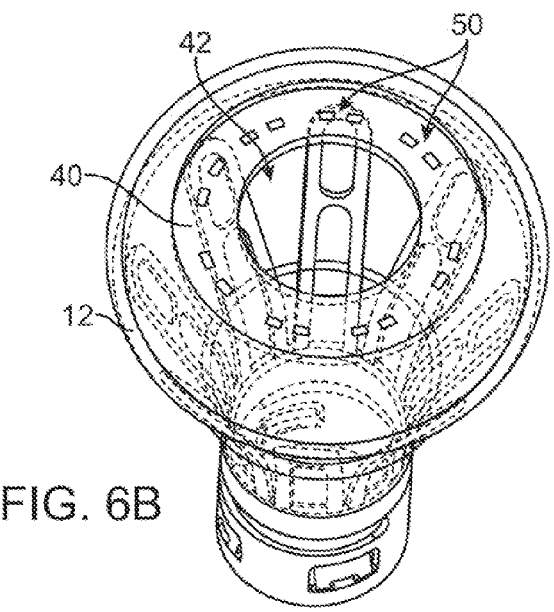
FIG. 6B shows a perspective view of another variation where one or more electrodes may be positioned circumferentially about the distal membrane surrounding the main aperture.
Figure 6C:
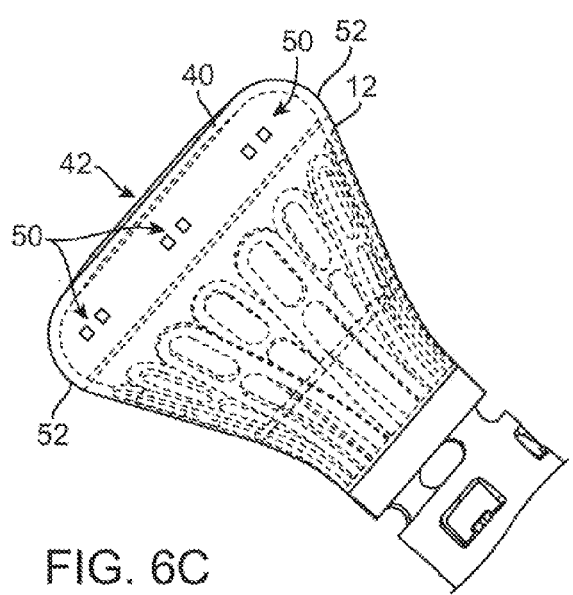
FIG. 6C shows a perspective view of another variation where one or more electrodes may be positioned circumferentially about a distal portion of the hood.
Figure 6D:
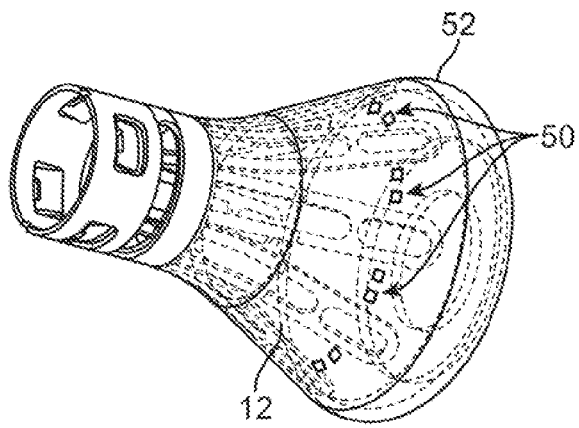
FIG. 6D shows a perspective view of another variation where one or more electrodes may be positioned circumferentially about a mid-portion of the hood.
Figure 6E:
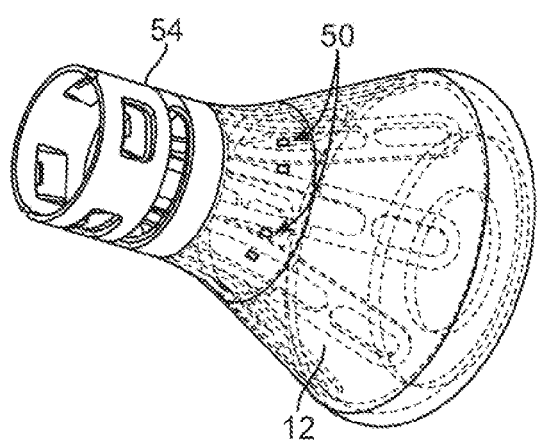
FIG. 6E shows a perspective view of another variation where one or more electrodes may be positioned circumferentially about a proximal portion of the hood.
Figure 6F:
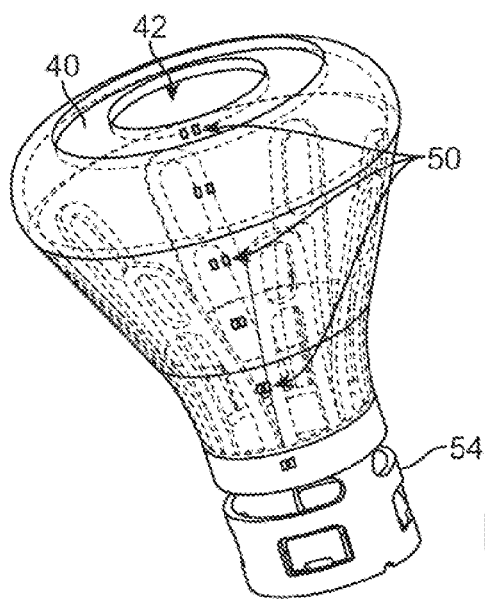
FIG. 6F shows a perspective view of yet another variation where one or more electrodes may be positioned along a length of the hood.

FIG. 6B shows a perspective view of another example where the one or more electrodes may be positioned upon the distal membrane 40 circumferentially about the main aperture 42. Another variation is shown in the view of FIG. 6C, which shows the one or more electrodes 50 positioned circumferentially upon a distal curved portion 52 of hood 12. FIG. 6D shows a perspective view of electrodes 50 positioned circumferentially about hood 12 proximally of the distal curved portion 52 while FIG. 6E likewise shows another variation where electrodes 50 are positioned circumferentially about hood 12 distal to the hood connecting member 54. FIG. 6F shows yet another variation where one or more electrodes 50 may be positioned along the hood 12 longitudinally between the main aperture 42 and connecting member 54.

Figure 7A:
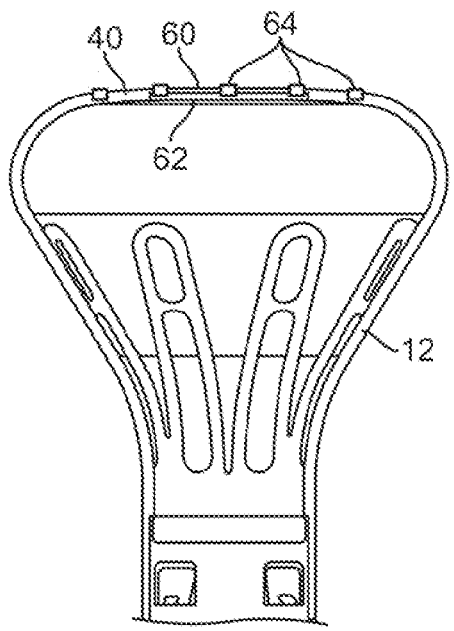
FIG. 7A shows a partial cross-sectional side view of another variation where one or more electrodes configured into various shapes, such as squares, rectangles, circles, etc., may be positioned about the distal membrane.
Figure 7B:
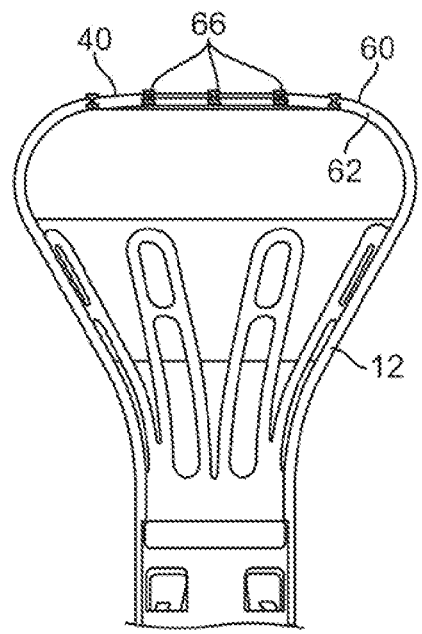
FIG. 7B shows a partial cross-sectional side view of another variation where one or more electrodes may be configured into an I-shape to facilitate securement of the electrodes within the distal membrane.

In positioning the electrodes along the hood, several methods may be used. FIG. 7A shows a partial cross-sectional side view of one example where electrodes 64 may be secured or adhered directly to the outer surface 60 of hood 12 as pads or contacts, e.g., shown illustratively along the distal membrane 40 although the electrodes 64 may be positioned elsewhere along hood 12. The one or more electrodes 64 may be formed into various shapes, e.g., square, rectangular, circular, triangular, etc. FIG. 7B shows another example where electrodes 66 may be I-shaped such that the electrodes extend between the outer surface 60 of the hood membrane and the inner surface 62. The upper portion of the I-shaped electrode 66 may extend radially out along the outer surface 60 while the lower portion of the electrode 66 may similarly extend radially out along the inner surface 62 such that the intermediate portion of the electrode 66 extends therebetween and is securely held in place between the outer 60 and inner 62 surfaces of hood 12.

Figure 7C:
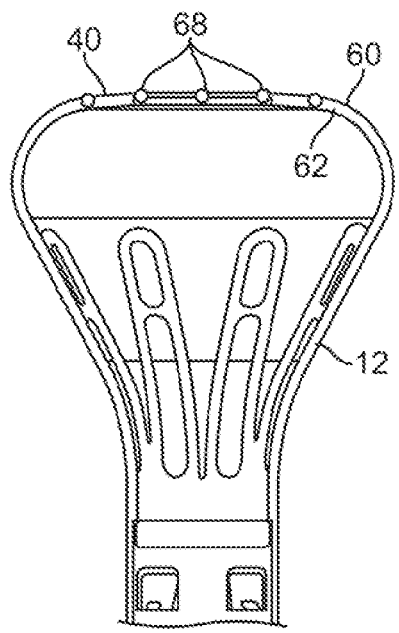
FIG. 7C shows a partial cross-sectional side view of yet another variation where one or more electrodes may be configured into a spherical shape projecting at least partially from the distal membrane.
Figure 7D:
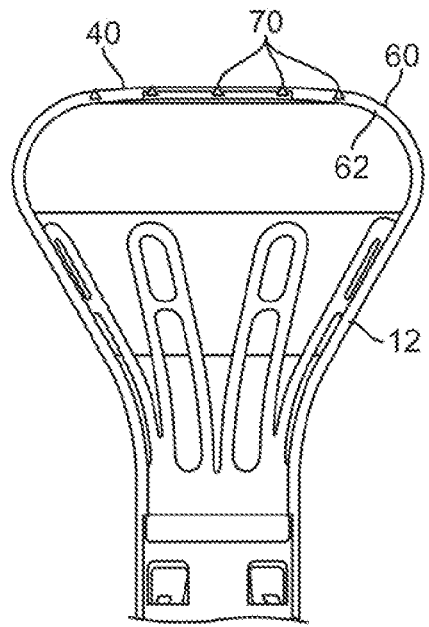
FIG. 7D shows a partial cross-sectional side view of yet another variation where the one or more electrodes may be configured into conical shapes having a distal tip projecting from the distal membrane to ensure securement of the electrodes within the distal membrane.

FIG. 7C shows a partial cross-sectional side view of another variation where spherically-shaped electrodes 68 may be integrated along the hood 12 such that a portion of the electrodes 68 is embedded within the hood 12 while a remainder projects distally from the hood outer surface 60. Yet another variation is shown in the side view of FIG. 7D, which illustrates conically-shaped electrodes 70 where the base portion of each electrode 70 may be embedded within the hood material while the apex of the electrode 70 extends past the outer surface 60 of hood 12 and projects distally for contact against or into proximity with the tissue to be treated. In this and the other variations, the electrodes are positioned upon or within the hood 12 such that they are securely attached thereto. Thus, while the hood 12 is collapsed and/or expanded, the one or more electrodes may remain securely adhered or attached to the hood 12.

Figure 8A:
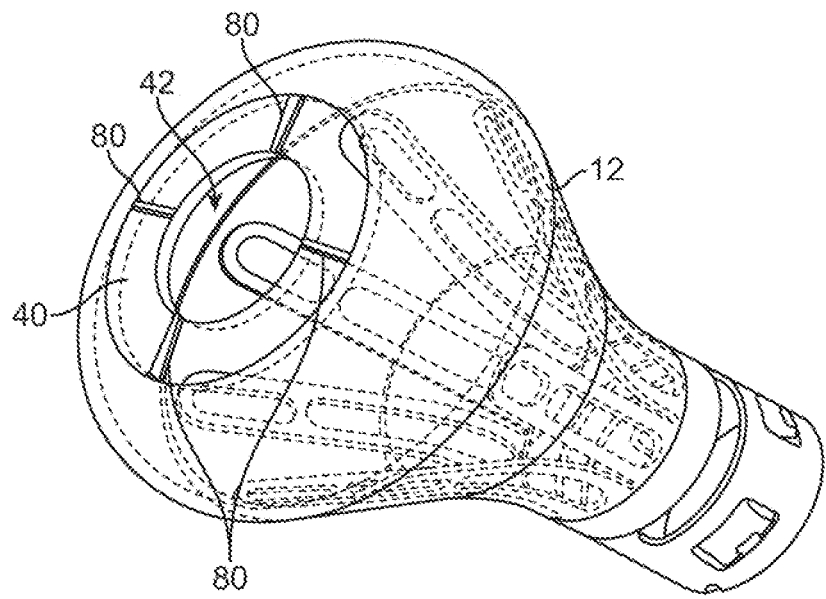
FIG. 8A shows a perspective view of another variation where electrodes may be configured into elongate elements which extend radially from the main aperture along the distal membrane.
Figure 8B:
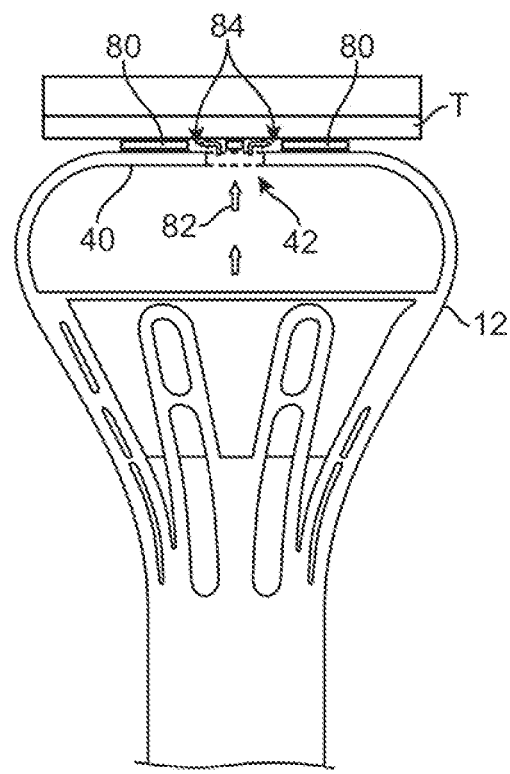
FIG. 8B shows a partial cross-sectional side view of the hood having radially extending electrodes positioned against a tissue surface.

Another variation is shown in the perspective view of FIG. 8A which illustrates one or more electrodes 80 which are shaped as elongate elements which extend radially from the main aperture 42 over the distal membrane 40. Although four electrodes 80 are illustrated, there may be fewer or more than four utilized. Each of the electrodes 80 may extend over distal membrane 40 and project distally from the surface of membrane 40. As shown in the partial cross-sectional side view of FIG. 8B, as the electrodes 80 are placed into apposition against the surface of a tissue region T to be visualized and/or treated, the electrodes 80 may form gaps 84 between the distal membrane 40 and tissue surface. As the purging fluid 82 is introduced into the hood interior and out through aperture 42, the fluid 82 may not only clear any blood from the gaps 84 to enhance visualization, but it may also conduct energy from the electrodes 80 for tissue treatment as well.

Figure 9A:
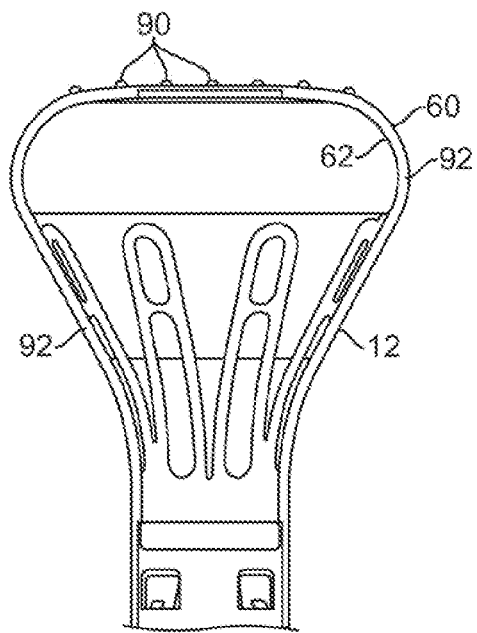
FIGS. 9A and 9B show partial cross-sectional side views of yet another variation where one or more inflatable members each having an electrode formed thereon may be inflated to project from the distal membrane.
Figure 9B:
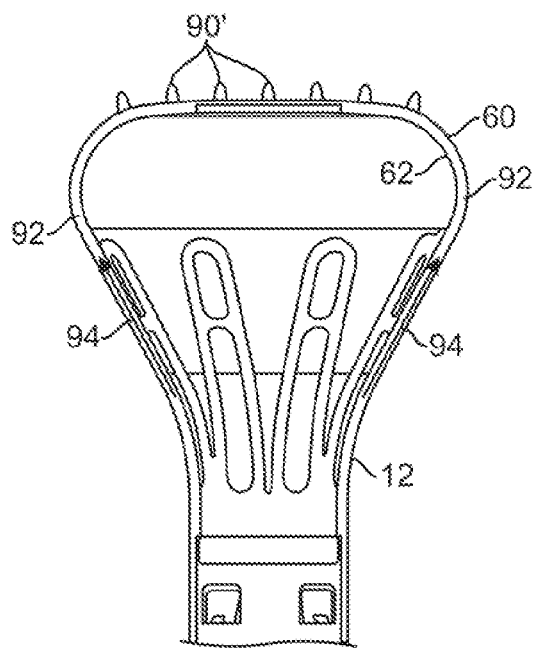

In yet other variations, FIGS. 9A and 9B show cross-sectional side views of a hood 12 having one or more electrodes 90 positioned upon expandable chambers defined along the hood outer surface 60. The expandable chambers, shown along the distal membrane, may each have an electrode 90 integrated thereon; moreover, each of the chambers may be expanded from a flaccid or unexpanded shape to an inflated configuration where the one or more chambers may be inflated via an inflation fluid or gas 94 passed through one or more inflation channels 92 defined between the outer 60 and inner 62 surfaces of hood 12. As the chambers are inflated, as shown in FIG. 9B, the electrodes 90 may be projected distally from the hood 12 such that the electrodes 90 are placed into direct contact against the underlying tissue while maintaining the hood a distance from the tissue surface. The one or more chambers may be fabricated from the same or similar material as the remainder of the hood 12.

Figure 10A:
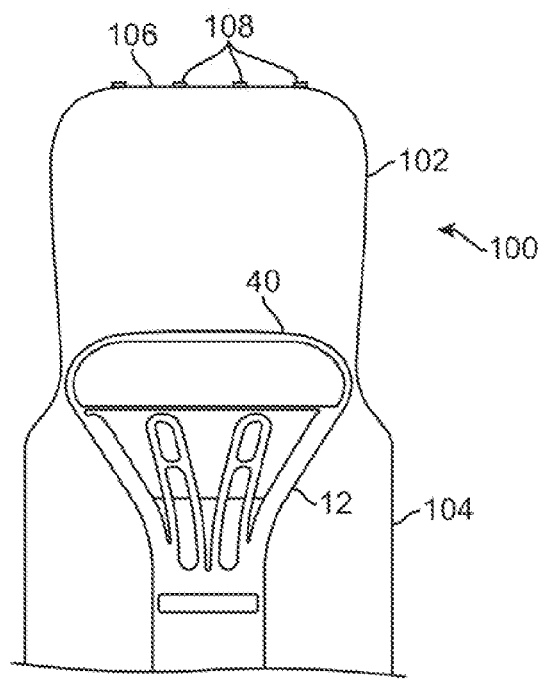
FIGS. 10A and 10B show partial cross-sectional side views of another variation which utilizes a flexible and/or distensible membrane having one or more electrodes formed thereon which may be slid over the hood.
Figure 10B:
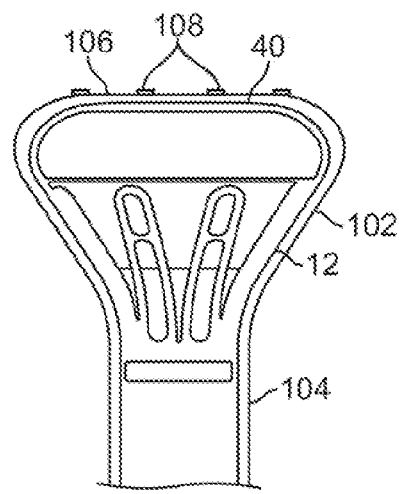

FIGS. 10A and 10B illustrate another variation where a covering assembly 100 comprised of a distensible, flexible, and/or scaffold-like material may be placed directly over the hood assembly. The covering assembly 100 may be comprised of a mesh-like or elastic material or the same or similar material as the hood 12 and have one or more electrodes 108 positioned upon a contact portion 106 of the covering which may slide upon the distal membrane 40 of hood 12. The distal portion 102 of covering 100 may also define an opening which is coincident with the main aperture of hood 12 to permit the exiting flow of the purging fluid. Moreover, portions of the covering 100 may be made to be more or less flexible than the remainder of the assembly. For instance, a proximal portion 104 of the covering 100 may be fabricated to be more flexible than the distal portion 102 to enable covering 100 to more closely conform to the contours of hood 12 and the catheter.

Another variation is shown in the side and cross-sectional end views, respectively, of FIGS. 11A and 11B. In this variation, because the electrode assembly may be advanced along the catheter and expanded hood independently, the electrode assembly does not experience the mechanical stresses of hood delivery and deployment. An expandable delivery channel 110 may be formed along the length of the catheter 16 and extend at least partially along the hood 12 such that a lumen 112 is defined through the length of the channel 110. An electrode assembly, for example, a reconfigurable ring electrode 116 advanced upon an electrode shaft 114, may be advanced through the length of the expandable channel 110 in a low profile and deployed distal to the hood 12 once the hood 12 has been desirably expanded, as illustrated in the side and cross-sectional views of FIGS. 12A and 12B.

Figure 13:
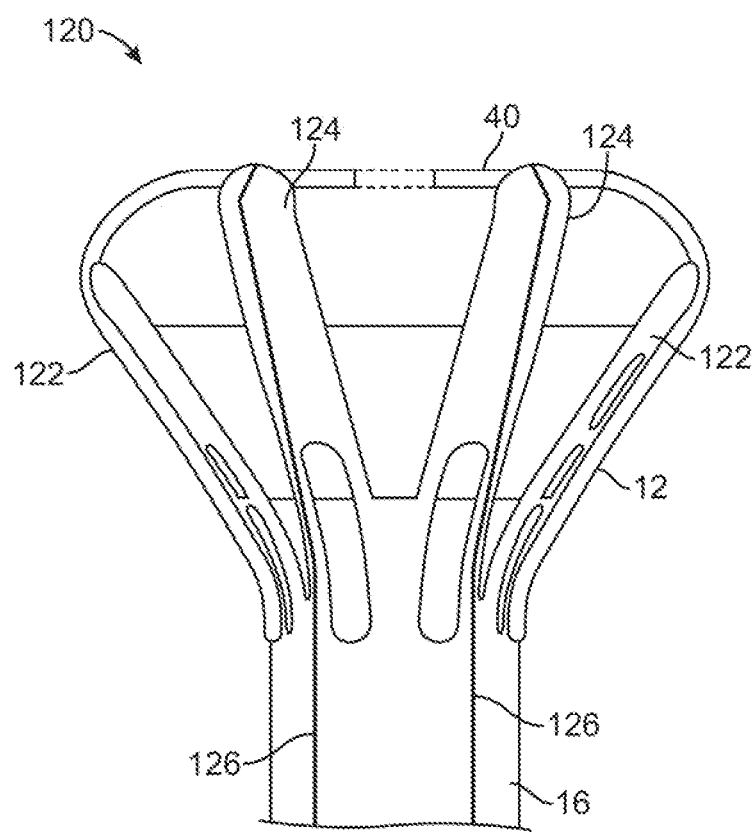
FIG. 13 shows a partial cross-sectional side view of yet another variation where one or more struts supporting the hood may extend towards the distal end of the hood to position corresponding electrodes along the distal membrane.

Another example is illustrated in the partial cross-sectional side view of FIG. 13, which illustrates a hood assembly 120 having one or more extended struts .124 which extend from the catheter 16 to the distal end of the hood 12. The one or more extended struts 124 may extend past the remaining struts 122 such that the distal ends of the extended struts 124 are flush with or project past the distal membrane 40 to contact the underlying tissue. The extended struts 124 may thus have electrodes positioned upon their distal ends for placement against the tissue while maintaining an electrical connection 126 through the struts 124. Utilizing the struts 124 as electrodes may take advantage of the robustness and strength provided by the struts 124 which are better suited to handle the mechanical stresses imparted upon the electrodes during hood delivery and deployment.

Figure 14A:
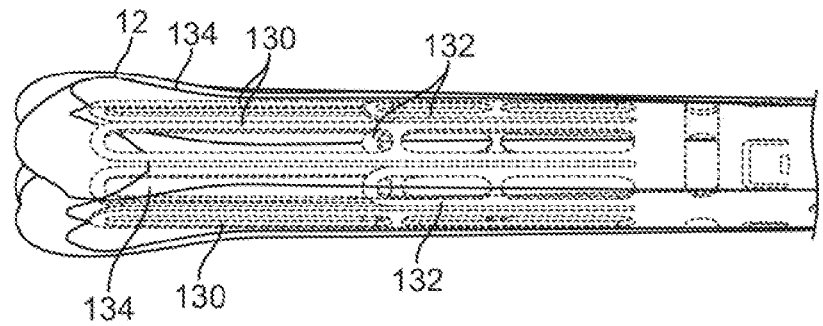
FIGS. 14A to 14C illustrate side, end, and perspective views, respectively, of another variation which utilizes struts of varying length to facilitate the folding or collapsing of the hood membrane into a low profile.
Figure 14B:
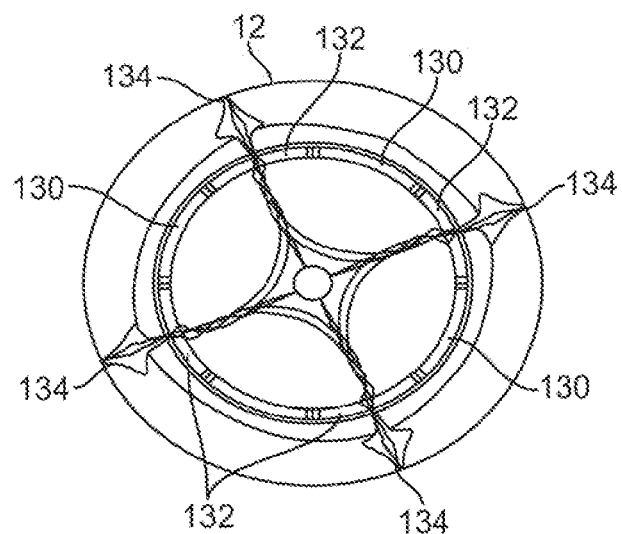
Figure 14C:
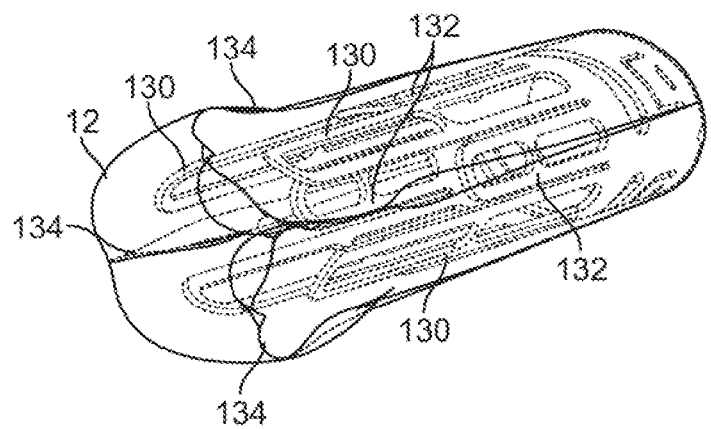

FIGS. 14A to 14C show another example in the side, end, and perspective views of another variation where the hood assembly may be configured to collapse or fold in a predetermined and consistent manner such that electrodes may be placed at locations upon the hood 12 which have a lower stress potential, e.g., along a portion of the hood 12 which is not folded for delivery or collapse. One mechanism for achieving this is to utilize struts of different lengths. For instance, struts 130 which extend along the hood 12 may be alternated with shortened struts 132 which are relatively shorter in length. The example shown illustrates shortened struts 132 which alternate with the longer struts 130; however, shortened struts 132 may be arranged in any number of other configurations if so desired. Because of the additional space created by the shortened struts 132 when hood 12 is collapsed, the collapsed portions 134 of hood 12 may collapse or fold consistently between the struts 130 along where the shortened struts 132 fold. Accordingly, with the hood 12 collapsing in a consistent folding pattern, electrodes or wires may be positioned along portions of the hood 12 which are not folded aside from the collapsed portions 134.

Figure 15A:
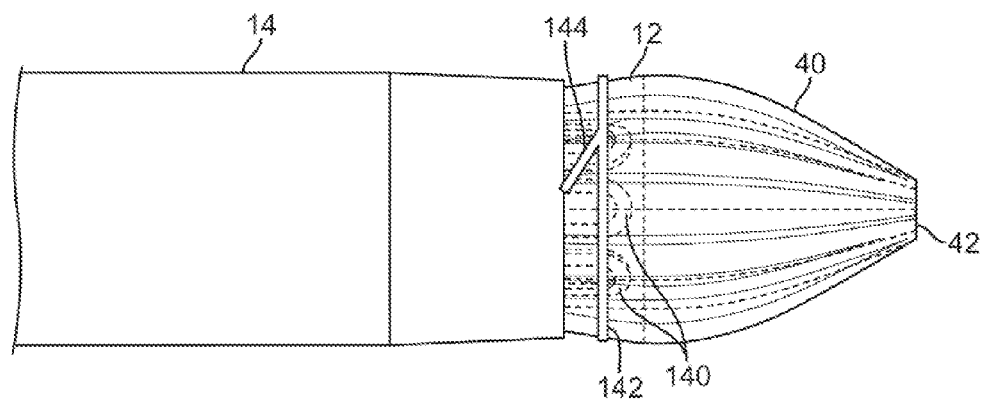
FIGS. 15A and 15B show side views, respectively, of another variation which utilizes a releasable cord to facilitate advancement and delivery of the collapsed hood.
Figure 15B:
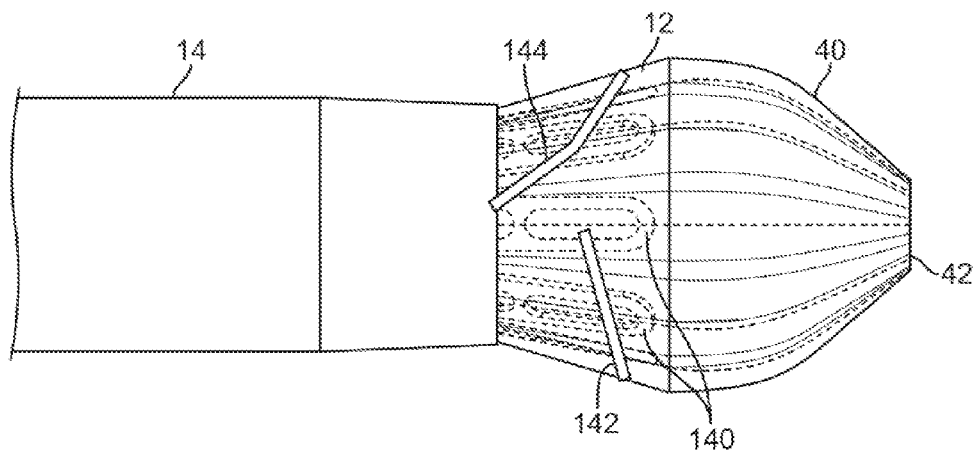

FIGS. 15A and 15B illustrate side views of another variation where a collapsed hood 12 may be initially folded and maintained in its collapsed configuration by a restraining member 142 prior to positioning the collapsed hood within the sheath 14. The maintenance of the hood 12 in its collapsed configuration allows for the initial retraction within the sheath 14 and subsequent deployment from the sheath 14 with a reduced stress load on the hood 12 as friction and sliding contact between the hood 12 and sheath 14 is reduced. Restraining member 142 may comprise a wire or ribbon which may be wrapped about the struts 140 of hood 12 to restrain the hood 12 from expansion. Once the hood 12 is ready to be deployed and/or expanded, hood 12 may be advanced from sheath 14 and a tensioning member 144 or release may be pulled or actuated to release the restraining member 142 from around the hood 12, as shown in FIG. 15B, e.g., by releasing a knot or simply breaking the restraining member 142. Restraining member 142 may be removed by pulling it proximally through sheath 14.

Figure 16A:
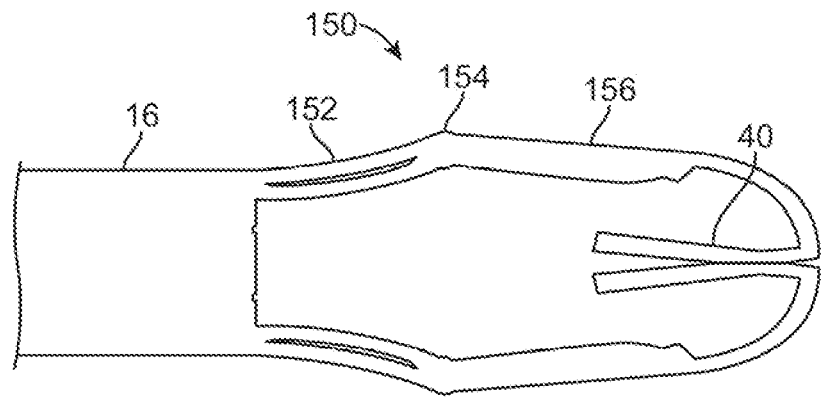
FIGS. 16A and 16B show partial cross-sectional side views of another variation of a hood utilizing struts which are preformed to have a bi-stable configuration between low profile and expanded shapes.
Figure 16B:
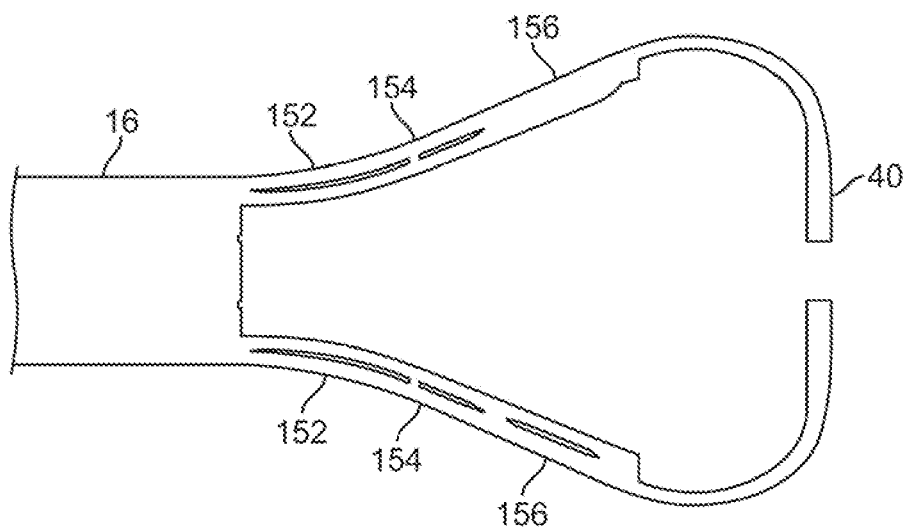

Another example is shown in the partial cross-sectional side views of FIGS. 16A and 16B, which illustrate a hood having a bi-stable strut assembly 150, i.e., struts which are preformed to have at least two mechanically stable configurations. A first configuration is shown in FIG. 16A where the struts may comprise a proximal portion 152, an intermediate hinged portion 154, and a distal portion 156 which collapses into a low profile when hood 12 is positioned within the sheath for delivery. When advanced distally for deployment or actuated via a mechanism (such as a push/pull wire), hood 12 may transition from its stable low-profile configuration into a second configuration which is also mechanically stable, as shown in FIG. 16B.

In maintaining electrical communication with the one or-more electrodes positioned at various locations upon the hood, electrical traces may be laid upon the hood 12 for maintaining electrical communication with the various electrodes. Such traces may be made of conductive materials through any number of methods, e.g., chemical vapor deposition, laser etching, micropen writing, adhesives, etc. Moreover, in laying down the traces upon or within the hood 12, the traces are desirably insulated along their lengths through any number of mechanisms. Additionally, use of traces placed within or along the hood 12 allows for added flexibility in connecting the electrodes along the hood to a power source and/or processor.

Figure 17A:
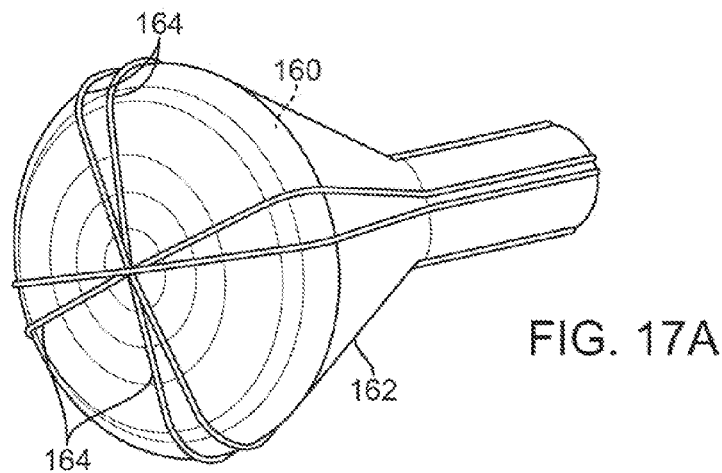
FIGS. 17A to 17C illustrate one example for forming a hood having integrated conductive members or traces formed within the hood material.
Figure 17B:
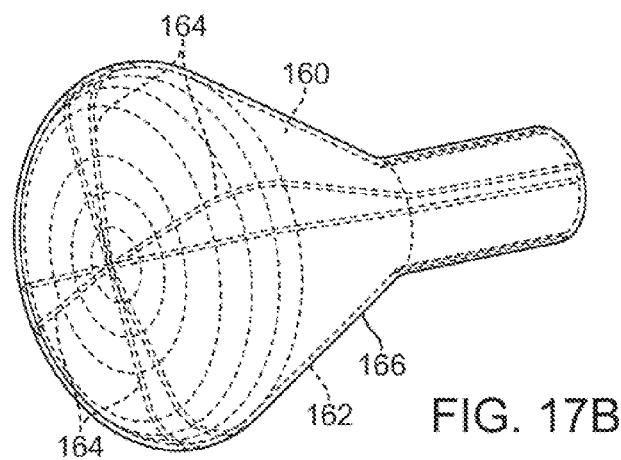
Figure 17C:
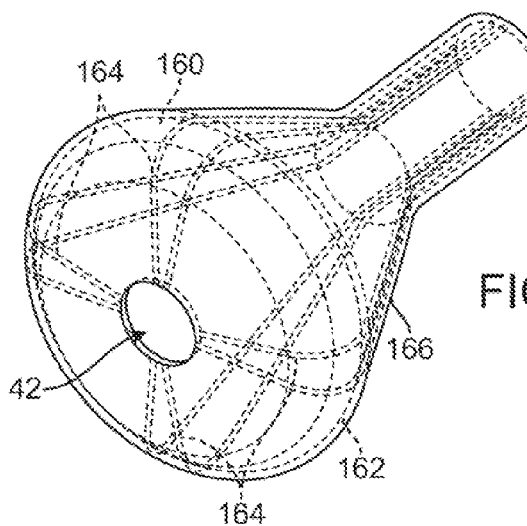

One example for utilizing electrical traces is illustrated in the perspective views of FIGS. 17A to 17C which show one variation for laying down traces integrated within a hood 12. By integrating the conductive traces within the hood itself, a robust electrical connection to the one or more electrodes may be maintained as the hood reconfigures between its low profile and deployed shapes. As shown, a mandrel 160 shaped in the form of the hood in its deployed configuration may be coated first with a first layer 162 such as an elastomeric material (e.g., silicone, chronoflex, polyurethane, etc.) which may be sufficiently dried or cured. One or more conductive traces 164 may be then laid upon the first layer 162 utilizing any of the methods mentioned and in any number of desired patterns extending along or over the first layer 162 and proximally along the mandrel 160 for electrical connection, as shown in FIG. 17A. With the conductive traces 164 sufficiently cured, a second layer 166 of material which may be the same or a similar material as the first layer 162 may then be laid atop both the first layer 162 and the conductive traces 164, as shown in FIG. 17B, to sandwich and electrical insulate the conductive traces 164 from the environment as well as from one another. With the second layer 166 of material cured or dried, the mandrel 160 may then be removed either physically or chemically from the conductive hood assembly.

In one variation, with a mandrel 160 made of a material such as acrylic, mandrel 160 may provide the desired structural support for building the layers of material and conductive traces 164 and when the mandrel 160 is to be removed, the entire assembly may be soaked in a chemical such as acetone to dissolve the mandrel 160 yet leave the first and second layers 162, 166 and sandwiched conductive traces 164 intact. With the mandrel 160 removed, the remaining hood structure may have one or more apertures, such as a main aperture 42, formed or cut into the distal membrane portion of the hood, as shown in FIG. 17C. Moreover, one or more electrodes may also be positioned anywhere along the length of the conductive traces 164 by exposing a corresponding portion of the underlying sandwiched trace.

This example as well as other examples for integrating the conductive traces within the hood itself may be utilized with any of the electrode configurations shown or described herein.

Figure 18A:
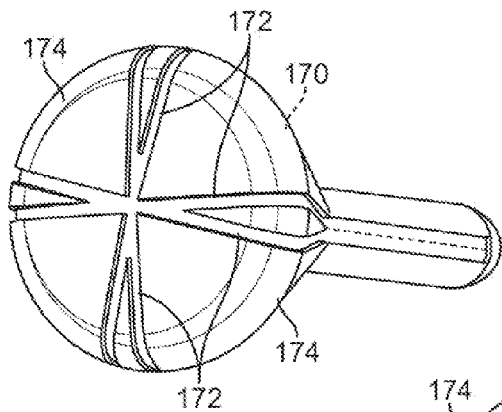
FIGS. 18A to 18D illustrate another example for forming a hood also having integrated conductive members formed upon a mandrel which defines one or more channels for the conductive members.
Figure 18B:
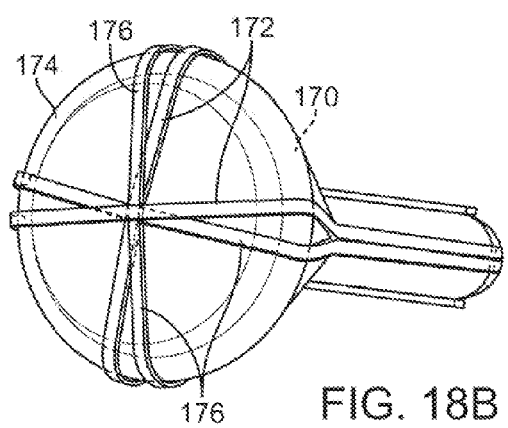
Figure 18C:
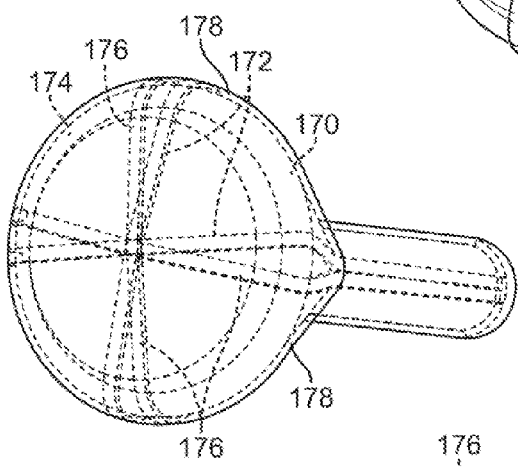
Figure 18D:
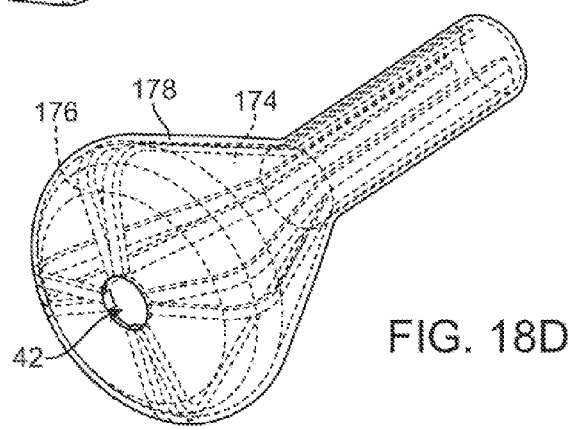

Another example of integrating conductive traces within the hood is illustrated in the perspective views of FIGS. 18A to 18D. As shown, a mandrel 170 similar to the previous example may be utilized to form the hood upon. In this variation, mandrel 170 may define one or more grooves or channels 172 along the mandrel surface to facilitate the formation of conductive traces within. FIG. 18A shows mandrel 170 having its grooves or channels 172 coated or covered by a first layer 174, as previously described. The one or more conductive traces 176 may be laid atop the first layer 174 within the grooves or channels 172 once the first layer 174 has sufficiently cured or dried, as shown in FIG. 18B. A second layer 178 of material, as previously described, may then be laid atop the first layer 174 as well as the conductive traces 176, as shown in FIG. 18C. Once the second layer 178 has sufficiently cured or dried, the mandrel 170 may be removed physically or chemically and the one or more apertures, such as main aperture 42 may be formed within the distal membrane portion, as shown in FIG. 18D. With this variation, the second layer 178 may form a smooth exterior hood surface despite the presence of the underlying sandwiched traces due to the flush formation of the traces within the depressed grooves or channels 172. By avoiding the formation of bumps or an irregular profile along the hood surface, the passage of the hood within or through an outer sheath may be facilitated.

Still referring to FIGS. 18A to 18D, yet another variation may utilize the assembly shown in which rods or other structures made from a dissolvable material, such as acrylic, may be laid within or along the length of the grooves or channels 172 and sandwiched between the first layer 174 and second layer 178. The resulting assembly, as shown in FIG. 18D, may then be soaked within a chemical such as acetone to dissolve not only mandrel 170 but also the encased rods or structures such that a cavity or lumen is formed through the hood where the grooves or channels 172 were initially defined. A conductive fluid may then introduced directly through the formed cavity or lumen to provide a conductive pathway for connection to the one or more electrodes.

Figures 19A, 19B:
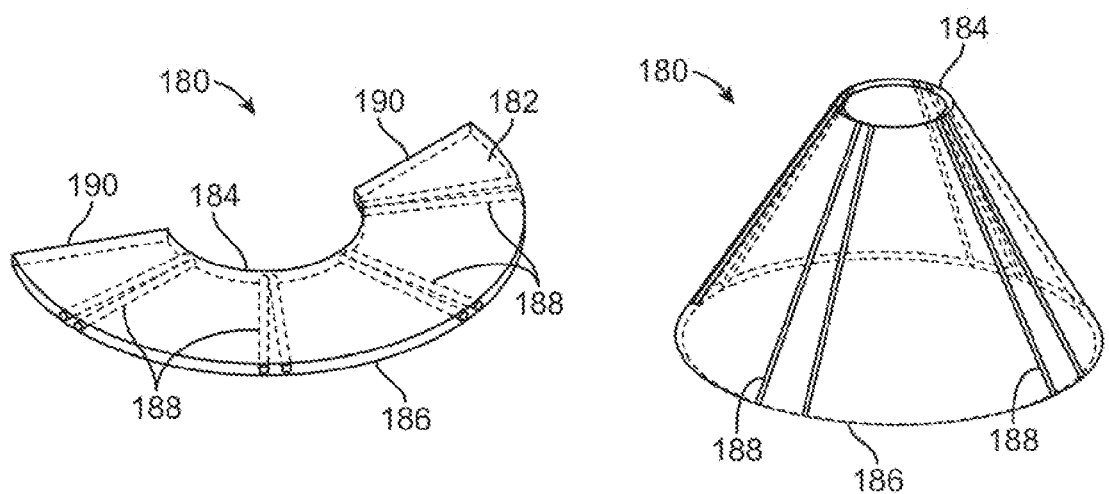
FIGS. 19A to 19C illustrate an example of a flattened substrate formed with conductive members extending radially and formed into a conical configuration for placement upon a mandrel for integration into a hood.

In yet another variation for forming conductive traces along the exterior or interior surface of the hood, FIG. 19A shows example of a flexible electrode assembly 180 formed of one or more conductive traces 188 which are encased or integrated within a polymeric substrate 182, which may be formed in a process similar to that described above. The assembly 180 variation shown illustrates a substrate which may be formed in the shape of an arc having a first inner radius 184 and a second outer radius 186. Although the conductive traces 188 are illustrated in a radial pattern extending between the first radius 184 and the second radius 186, any number of patterns may be utilized depending upon the desired positioning of the one or more electrodes along the hood.

Figure 19C:
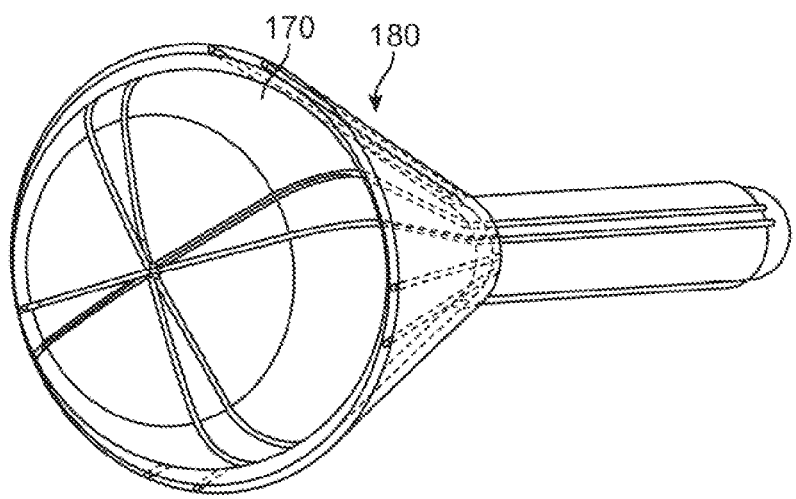

The terminal edges 190 of the substrate may be joined, as shown in the perspective view of FIG. 19B, to form a conical structure which may then be laid atop a mandrel 170 for subsequent coating by additional layers of elastomeric material, as shown in the perspective view of FIG. 19C and as previously described. This particular variation may facilitate the manufacturability of the hood having integrated conductive traces within. The hood can also be formed with electrodes in a single layer through a process called insert molding. The flex circuit ay be held in or near the center of the silicone wall by projections from the cavity and core of the injection mold tool and silicone or other elastomer may be molded around the flex circuit or electrode assembly. The projections leave holes in the elastomer which will be closed or alternately, the projections could contact the flex circuit on its exterior side where there are electrodes and/or on its interior surface by contacting on non-conductive portions of the flex circuit. In yet another variation, the flex circuit may have silicone projections molded onto it at selected locations in a first operation. The silicone projections may then hold the flex circuit when it is loaded into a mold tool in or near a center of the injection mold tool (e.g., between the mandrel and the cavity of the tool) so that silicone can be molded around it. As previously mentioned, this as well as other examples for integrating conductive traces within or along the hood assembly may be utilized within any of the electrode positioning embodiments described herein.

Figure 20A:
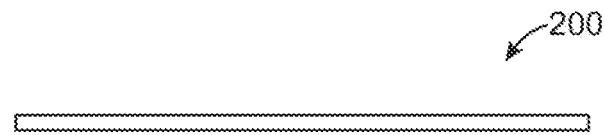
FIGS. 20A to 20D illustrate various examples of configurations which the conductive members or traces may be formed for placement upon or integration alone a hood.
Figure 20B:
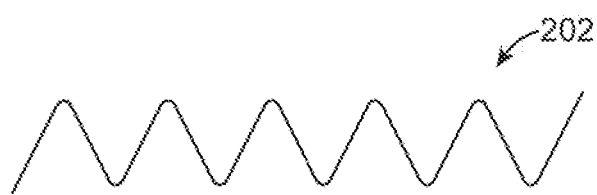
Figure 20C:
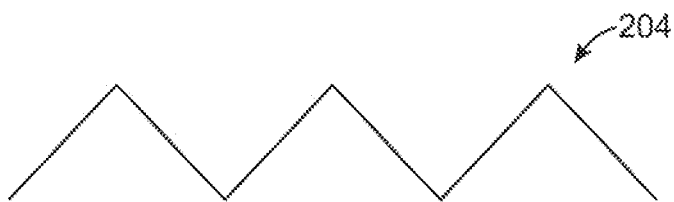
Figure 20D:
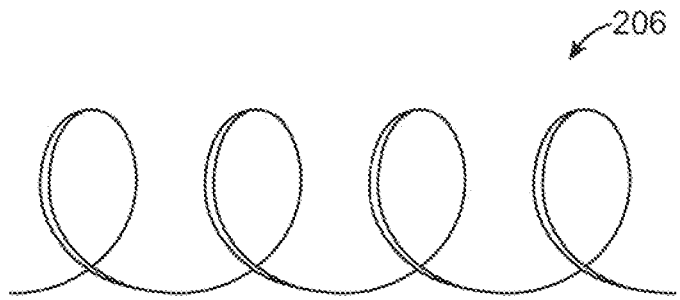

Turning now to the trace connections which connect the electrodes to the power supply and/or signal processor (or any other unit), such traces are desirably robust enough to withstand the high mechanical stresses which are imparted to the traces as the hood undergoes introduction and removal from the sheath as well as the reconfiguration between its low profile and deployed profile. As such, the traces may be laid in any number of patterns which may alleviate the stresses imparted to the traces. Traces may accordingly be laid in, e.g., straight patterns 200 (as shown in FIG. 20A), or curved patterns 202 (as shown in FIG. 20B). Alternatively, the traces may also be laid in, e.g., saw-tooth patterns 204 (as shown in FIG. 20C), or even looped and/or helical patterns 206 (as shown in FIG. 20D), which may allow for expansion and/or contraction of the trace without breaking or losing electrical continuity through the trace. These examples are, of course, intended to be illustrative of certain examples for trace patterns and are not intended to be limiting.

Figure 21A:
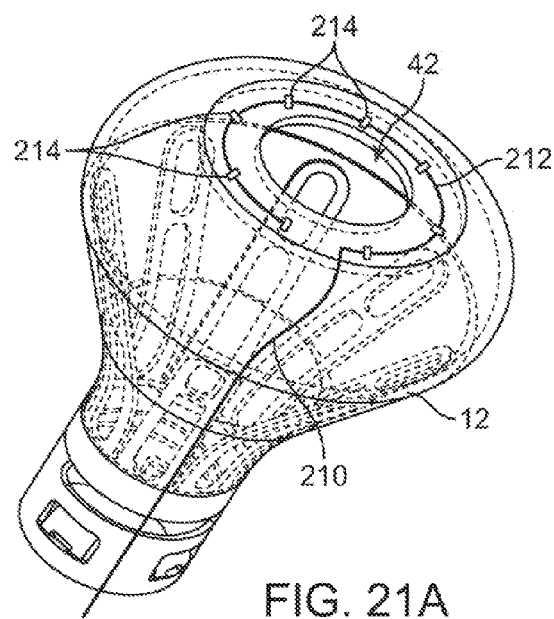
FIGS. 21A and 21B illustrate perspective views of examples for positioning of a conductive wire assembly upon the hood.
Figure 21B:
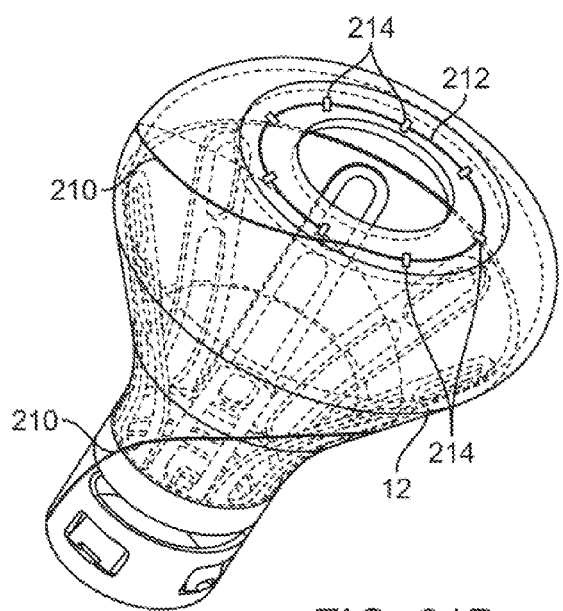

Aside from use of conductive traces, alternative mechanisms for maintaining robust electrical communication to electrodes positioned on a deployable hood may utilize conducting wires which are structurally robust enough to endure the stresses imparted on them. One example is shown in the variation of FIG. 21A, which illustrates a perspective view of a deployed hood 12 with a conductive cable assembly 210. Cable assembly 210 may be positioned to extend along the length of hood 12 to form a looped portion 212 at least partially encircling the main aperture 42. Looped portion 212 may comprise one or more exposed electrode segments 214 for contact against the underlying tissue. FIG. 21B shows a perspective view of another variation where cable assembly 210 may be wrapped about hood 12 in a helical pattern, such that looped portion 212 terminates about main aperture 42 to alleviate mechanical stresses imparted upon assembly 210 during hood reconfiguration.

Figure 21C:
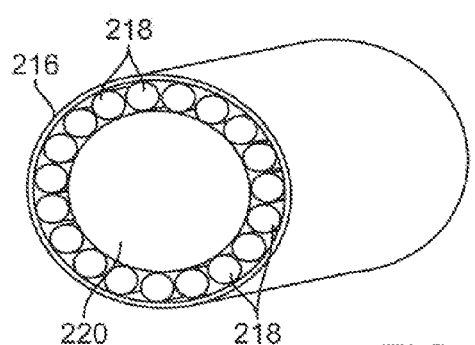
FIG. 21C illustrates a detailed cross-sectional perspective view of the conductive wire assembly having a cable core surrounded by one or more conductive wires.
Figure 22A:
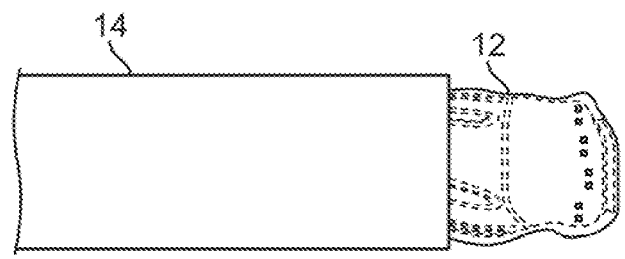
FIGS. 22A to 22D illustrate another example of an expandable hood having a separate electrode assembly advanced through the hood interior.
Figure 22B:
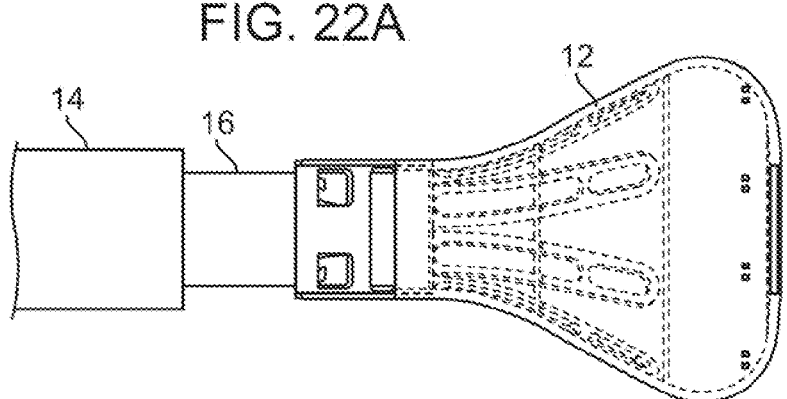
Figure 22C:
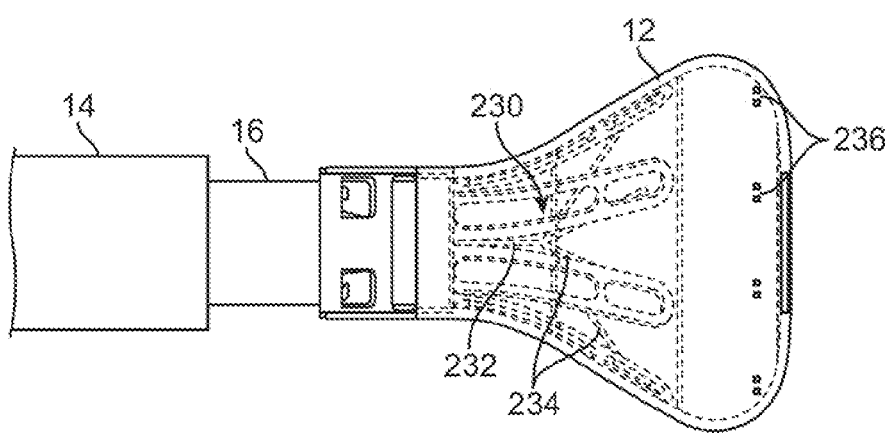
Figure 22D:
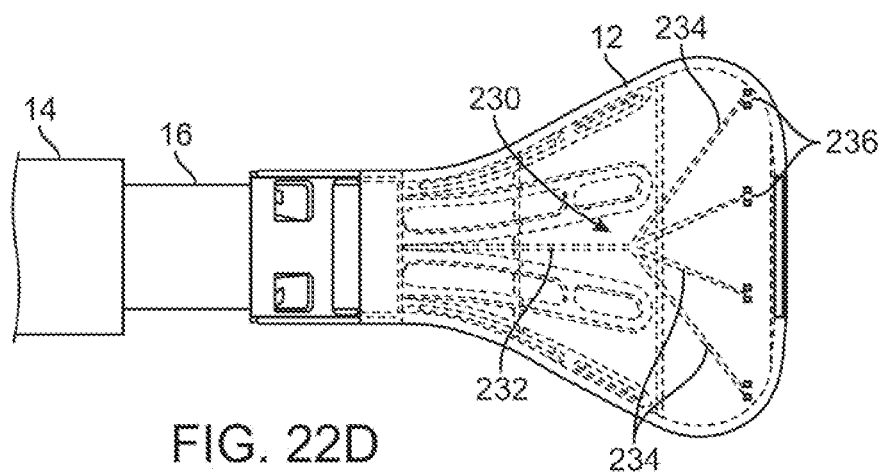

In forming a mechanically and electrically robust cable assembly 210, the cable may generally comprise a core wire 220 having a first diameter which provides mechanical strength to the assembly 210, as shown in the detailed cross-sectional perspective view of FIG. 21C. Core wire 220 may be surrounded by individual lengths of adjacent conductive wires 218 each of which have a second diameter which is smaller than the first diameter of the core wire 220. The entire assembly may be encased by an insulative outer covering 216 which may be exposed at regions where electrode segments 214 are positioned.

Another variation for forming a robust system for maintaining electrical communication is shown in the side views of FIGS. 22A to 22D. In this variation, the one or more electrodes may be disposed upon the hood but the electrical connection to the electrodes may be deployed separately from the hood deployment. As illustrated in the side views of FIGS. 22A and 22B, hood 12 may be advanced from sheath 14 from its low profile and deployed into its expanded profile. An expandable electrode assembly 230 separate from the hood 12 may then be advanced through catheter 16 and into hood 12. Electrode assembly 230 may generally comprise a conductive support member 232 having one or more conductive branching members 234 which are reconfigurable from a low profile configuration, where each of the branching members 234 are compressed, to an expanded configuration, where several branching members 234 may reconfigure into a deployed configuration. Each of the deployed branching members 234 may extend at an angle such that the members 234 come into electrical contact with corresponding electrode pads 236 positioned along the hood 12, as shown in the side views of FIGS. 22C and 22D. By separating the hood 12 from the electrical conductor assembly, the connection system is not subjected to the mechanical stresses normally imparted by the reconfiguring hood 12.

Figure 23A:
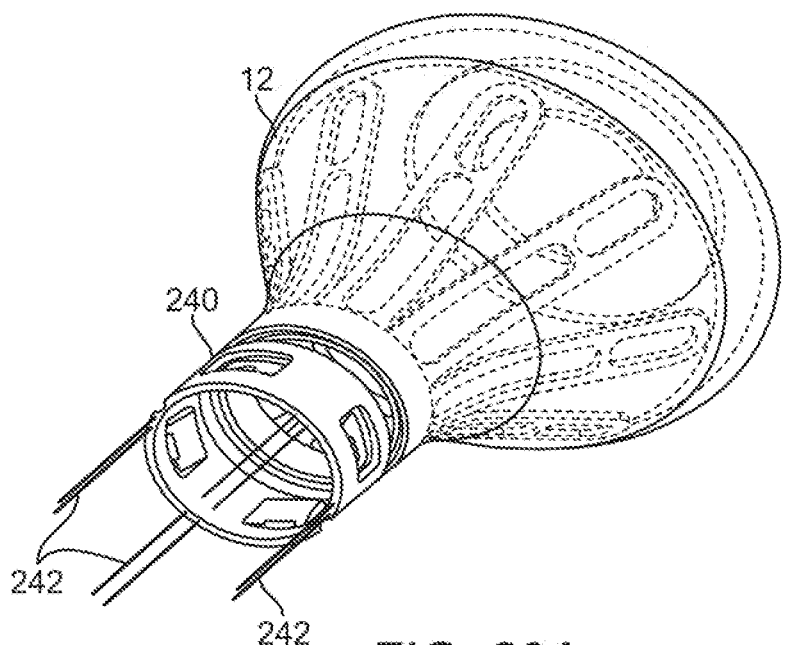
FIG. 23A shows a perspective view of another example where a hood assembly having integrated electrodes may utilize connector pins for securement and electrical contact with a receiving assembly defined along the advancement catheter.
Figure 23B:
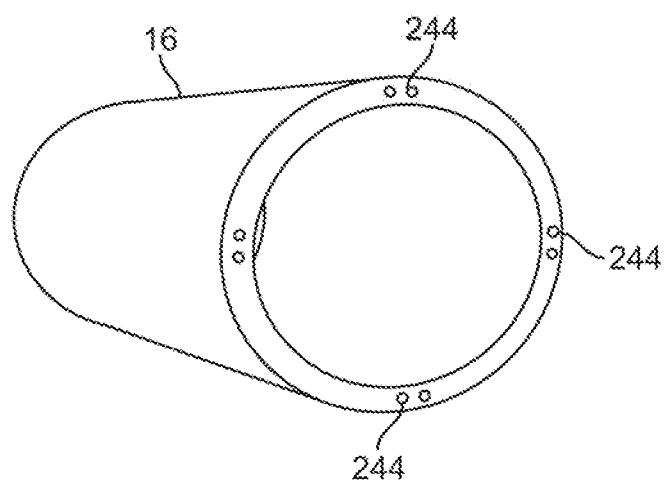
FIG. 23B shows a perspective view of a catheter distal end having corresponding connector slots for receiving the connector pins of the assembly of FIG. 23A.

In addition to the electrical connections to the electrodes positioned on the hood, termination of the connection systems from the hood assembly and to or through the delivery catheter 16 is also a consideration as electrical isolation, robustness, ease of manufacturability, etc. are of concern as well. Turning now to the perspective view of FIG. 23A, one variation of a hood assembly having a connector base 240 is shown with one or more electrode connector pins 242 projecting from the connector base 240. The one or more connector pins 242 may be electrically coupled to one or more corresponding electrodes positioned within or along the hood 12 The hood assembly may be connected, electrically as well as mechanically, to the catheter 16 by the insertion of connector pins 242 into one or more electrode receiving slots 244, as shown in the perspective view of FIG. 23B, which may be in electrical communication with a power supply and/or processor through the length of the catheter 16. The insertion and coupling of the connector pins 242 with the receiving slots 244 helps to ensure a secure electrical and mechanical connection as the hood 12 is delivered and deployed.

Figure 24:
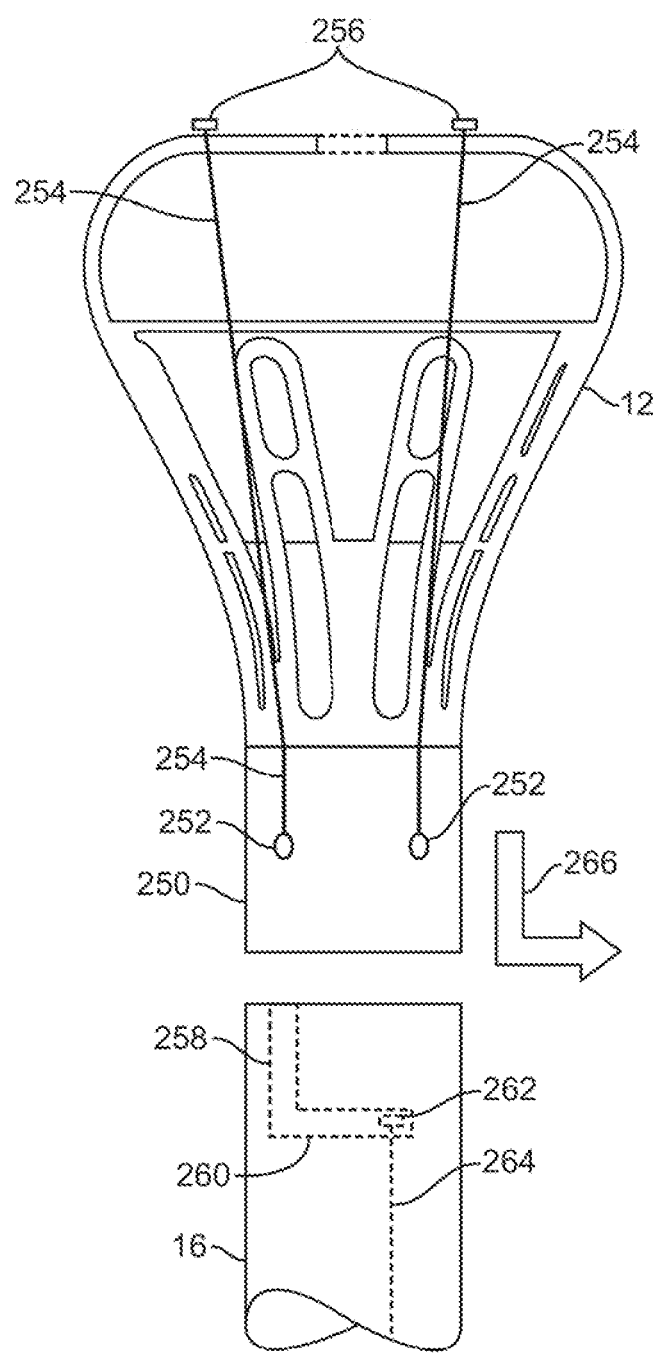
FIG. 24 shows a partial cross-sectional side view of a hood assembly having one or more conductive projections which may slide and lock into a receiving channel defined along the catheter distal end.

In yet another variation, FIG. 24 shows a partial cross-sectional side view of a hood assembly having a connector base 250 with one or more conductive studs or projections 252 extending from the base 250. Each conductive stud or projection 252 may be electrically coupled via conductive wires 254 to one or more corresponding electrodes 256 position within or along hood 12. Because the studs or projections 252 extend from a surface of the base 250, a receiving channel 258 may be defined longitudinally along the distal end of the catheter 16. The receiving channel 258 may further define a locking channel 260 which extends from receiving channel 258 at an angle, e.g., perpendicularly, such that as the base 250 of the hood assembly is coupled to catheter 16 the base 250 is forced to be twisted as the one or more projections 252 are guided along receiving channel 258 and then along the angled locking channel 260. This direction of movement, as indicated by locking direction 266, may force the one or more projections 252 into secure contact against one or more corresponding conductive contacts 262 which may be in electrical communication through catheter 16 via corresponding conductive wires 264. Moreover, the twisting of the hood assembly relative to the catheter 16 further helps to ensure rigidity of the coupling as well as electrical isolation between electrodes.

Figure 25:
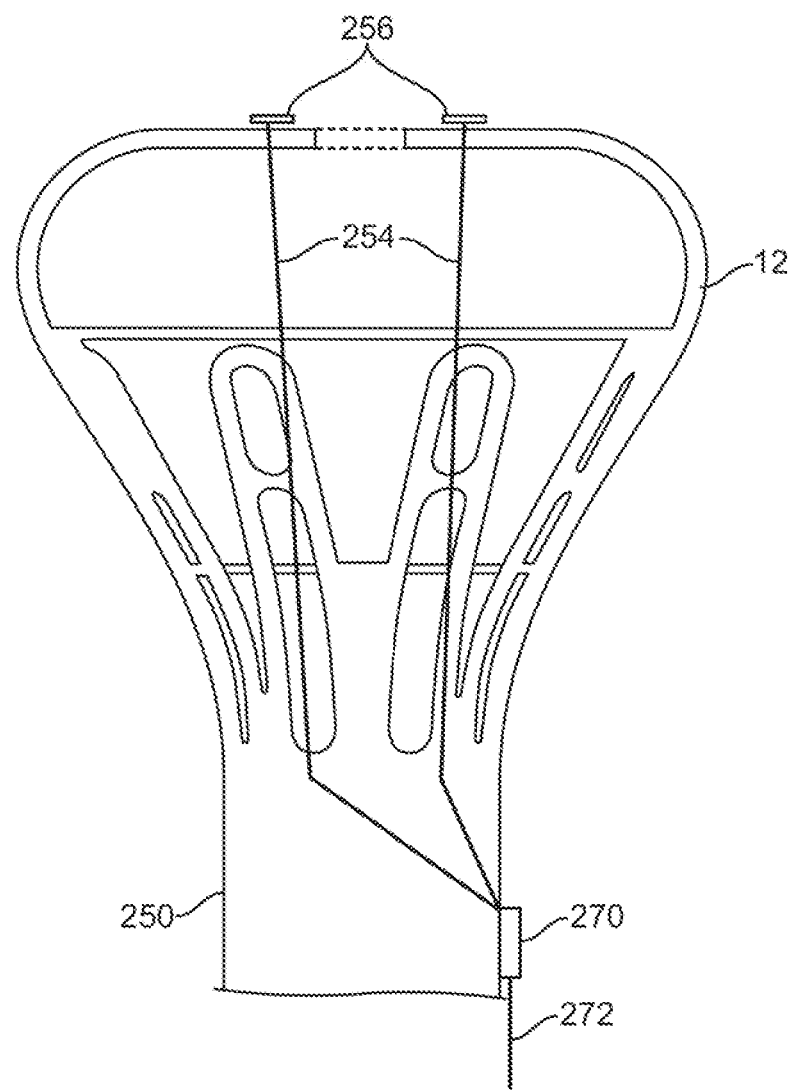
FIG. 25 shows a partial cross-sectional side view of another hood assembly having integrated electrodes electrically coupled to a processor which may be integrated directly into the hood assembly.

In yet another example, rather than having conductive wires transmit signals to and from the one or more electrodes within or along the hood and to a power supply or processor located separately from the catheter assembly, the electrical connection systems to and from the electrodes may be terminated locally along the hood assembly itself. As shown in the cross-sectional side view of FIG. 25, the electrodes may be electrically coupled to a local signal processor 270 attached, e.g., to the base 250 of the hood assembly. The signal processor 270 may generally comprise at least a single microprocessor for processing and outputting any received and processed signal through a single wire 272 passed through the catheter. Such a design may facilitate the electrical connection to the electrodes as well as facilitate the manufacturability of the hood assembly by reducing the number of connecting wires.

Any of the electrode assemblies show and described herein may be utilized for various purposes aside for the delivery of ablation energy. For example, the electrode assemblies may be utilized for detecting or sensing electrical energy transmitted through the underlying tissue of interest. Such electrodes may be used to detect or sense the electrical energy naturally conducted through the body for electrocardiogram measurements, cardiac pacing, etc., prior to tissue treatment for electro-anatomical mapping (e.g., as described in U.S. Pat. No. 7,263,397 which is incorporated herein by reference in its entirety). Alternatively, these signals may be detected during a tissue treatment or after for determining the efficacy of a treatment, e.g., ablation energy delivered into the tissue for creating a conduction block.

The structure of the circuit assembly for forming and/or connecting the electrodes along the hood structure can generally be one of two types. In a first example, most or all of the electrodes may be formed on a single circuit element while in a second example, most or all of the electrodes may be formed onto multiple circuit elements. In this latter form, the multiple elements may be configured in the same manner, but may be of a limited number of types; for instance, one type of element may be used for detecting or sensing electro-anatomical mapping while another type may be used for detecting or sensing electrocardiograms.

Figure 26A:
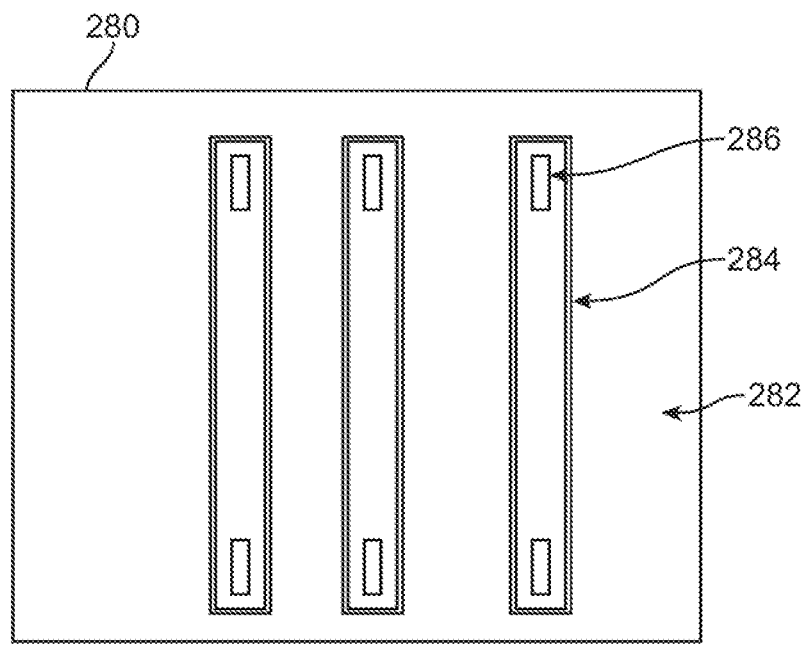
FIGS. 26A and 26B show top and cross-sectional side views, respectively, of an example of the construction of an electrode array fabricated as a flexible printed circuit for integration within or along a hood assembly.
Figure 26B:
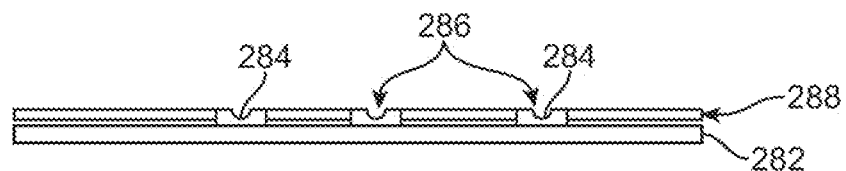

The use of wafer, roll, or sheet scale manufacturing for producing electrical circuit traces may be used to form large quantities of flat, flexible-circuits that may be incorporated in the hood. In one variation shown in the top and cross-sectional side view of FIGS. 26A and 26B, electrical traces 284 may be laid upon sheets or rolls of a flexible polymeric base layer 282 such as polyimide (e.g., Kapton®, E.I. Du Pont De Nemours, DE), polyester (e.g., Mylar®, E.I. Du Pont De Nemours, DE), or liquid crystal polymer (e.g. Xydar®, Dart Industries, Inc., IL), etc., via processes used in the fabrication of printed circuit boards. Such sheets 280 can be readily obtained in thicknesses as small as 25 µm. The polymer base layer 280 and its traces 284 may then be covered in at least a second sheet of a polymer overcoat layer 288.

This deposition and covering process can be repeated to form multiple different layers of conductive traces. One or more vias 286 can be placed between or through different layers to allow traces 284 from one layer to electrically access other layers of the assembly 280 and the top-most or bottom-most polymer layers may also have vias 286 created to expose the underlying conductive traces 284. Additionally, localized areas may be stiffened by the addition of additional polymeric material in those areas.

Figure 27:
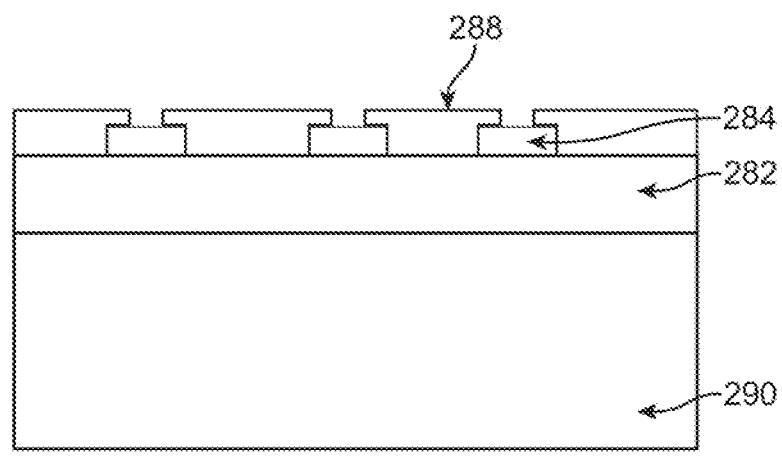
FIG. 27 shows another example of an electrode array patterned by the deposition of conductors and insulators atop of a rigid substrate.

In another variation shown in the cross-sectional side view of FIG. 27, curable polymeric materials such as polysilicone, etc., may be deposited onto a relatively stiff substrate 290 via any number of methods such as spin coating, dip coating, mechanical spreading, etc. The thickness of the polymeric base layer 282 may be controlled by the deposition method and may range, e.g., from 25 µm to 100 µm. Conductive traces 284 may then formed on the base layer 282 by a variety of methods including vapor deposition, electroplating, etc. Furthermore, the conductive traces can be formed from conductive polymers, such as silver-bearing polysilicones. Once the patterned traces 284 have been formed, an insulating layer 288 may be deposited and one or more vias or openings 286 may be created in the insulating overcoat layer 288 to expose areas of the conductive traces 284 below. These opening may be created by myriad methods know to those skilled in the art, such as patterned deposition, chemical etching, laser milling, etc. This process of metal deposition and insulation coating may be repeated to form multiple layers of circuits. After completion, the formed stack of polymer layers can then be removed from the relatively rigid substrate 290 and further processed, if desired or necessary, into the final configuration.

Figure 28:
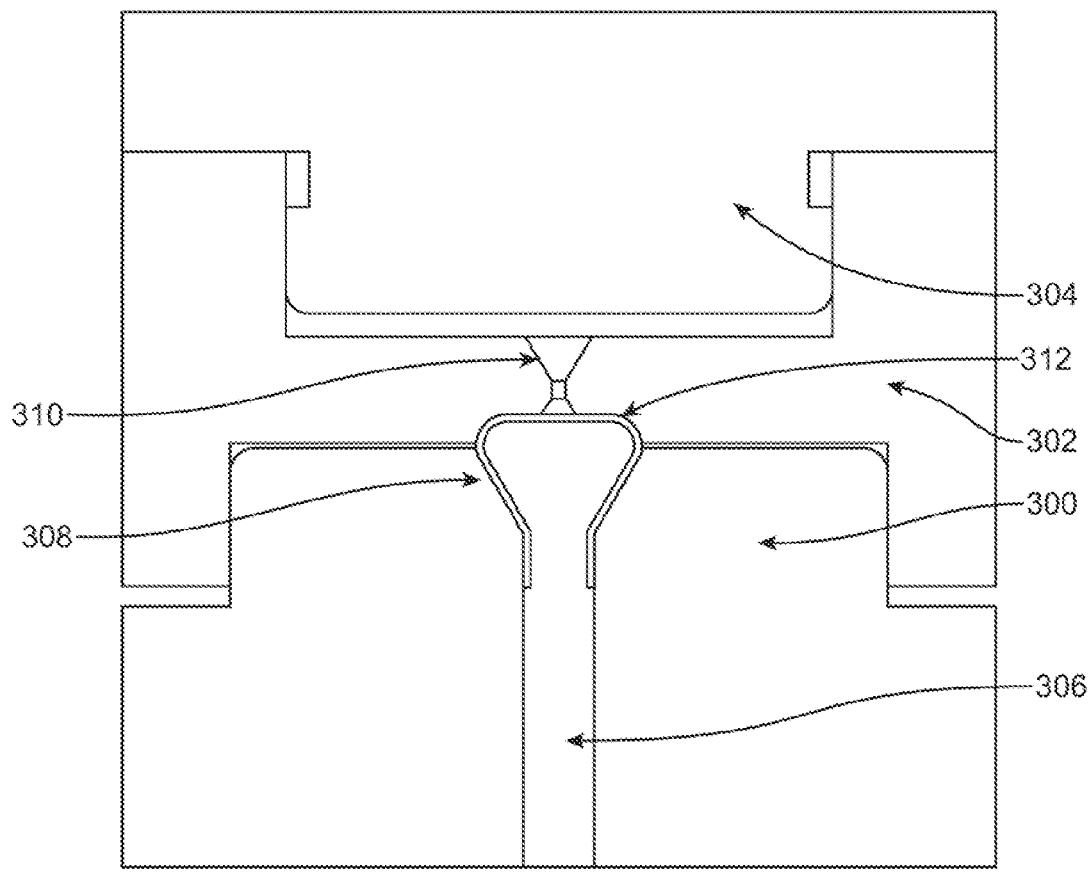
FIG. 28 shows another example of manufacturing an exemplary hood assembly with integrated electrodes by overmolding of an insulating polymer on a semi-rigid frame.

Once the layers and traces have been formed, individual circuit elements can be singulated from the array of elements and the circuit elements can then be incorporated into the assembly of the hood. In one exemplary process, the hood 12 may be formed by molding, e.g., silicone, where the circuit assembly can be introduced into the surface of the mold and the mold filled with silicone to create a combined assembly. FIG. 28 shows a cross-sectional side view of an exemplary molding assembly for creating such a hood having an integrated flexible circuit assembly. In this example, a base mold 300 may define a partial cavity 308 for receiving the proximal end of a hood-shaped mandrel 306 which when positioned within the partial cavity 308 defines an annular space between the mandrel 306 and cavity 308 for forming of the hood itself. The formed flexible circuit assembly 312 may be positioned upon the mandrel 306 and a second mold 302 defining a complementary receiving cavity may be aligned with the base mold 300 such that the mandrel 306 is positioned between both molds 300, 302 which form the annular space for formation of the hood therein.

A third mold 304 may be positioned upon the second mold and the silicone material, in liquid form, may be flowed into the annular space from between the second mold 302 and third mold 304 through one or more openings 310 defined through the second mold 302 in communication with the annular space. As the mold is compressed, the silicone may be flowed through openings 310 and into the annular space formed between the mandrel 306 and the base mold 300 and second mold 302. The resulting hood may have the flexible circuit assembly 312 integrated with the hood structure and the circuit assembly 312 may also provide some structural stability to the hood in its delivery and deployed configurations.

Additionally and/or optionally, the hood may also incorporate a semi-rigid frame to provide some stability to the shape of the hood structure. In this case, it may be desirable to bond the flexible circuit assembly 312 to the frame prior to over-molding with polymer.

During the over-molding process, the metal contacts or electrodes in the circuit assembly may remain exposed such that these contacts remain uncovered by the insulating hood material. This can be accomplished through different methods, e.g., the use of vacuum ports in the mold aligned with the exposed contacts, the attachment of conductive pins, studs, balls or similar structures at the contact points, or coating the exposed contacts in a sacrificial material such as polymethmethacrylate (PMMA) and subsequent removal of the sacrificial material after the completion of the over-molding process.

Figure 29A:
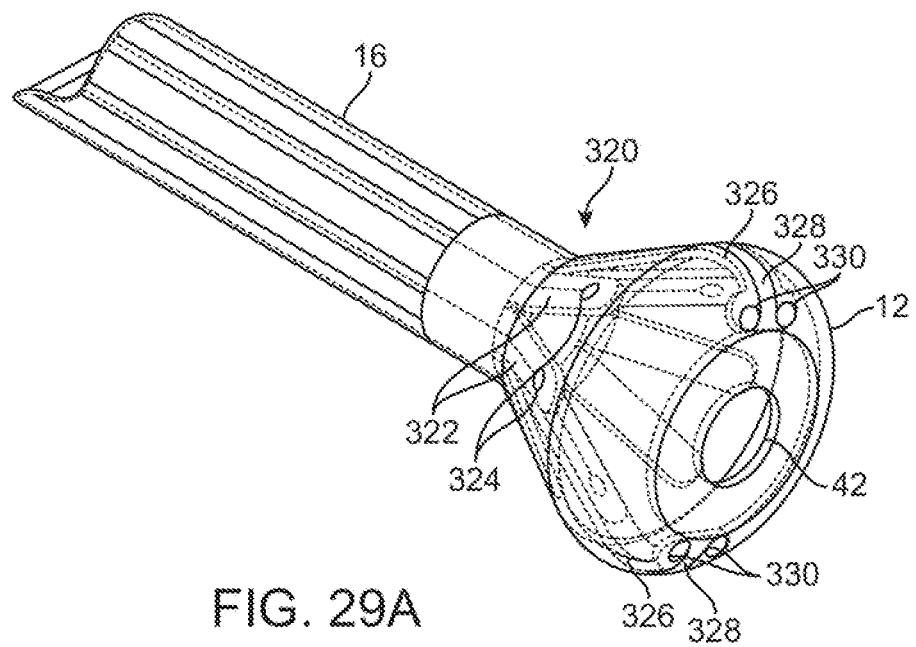
FIGS. 29A and 29B show perspective views of an electrode array assembly positioned along the hood and extending distally at least partially upon the distal membrane with electrodes which are flush as well as raised for improving contact with the tissue surface.
Figure 29B:
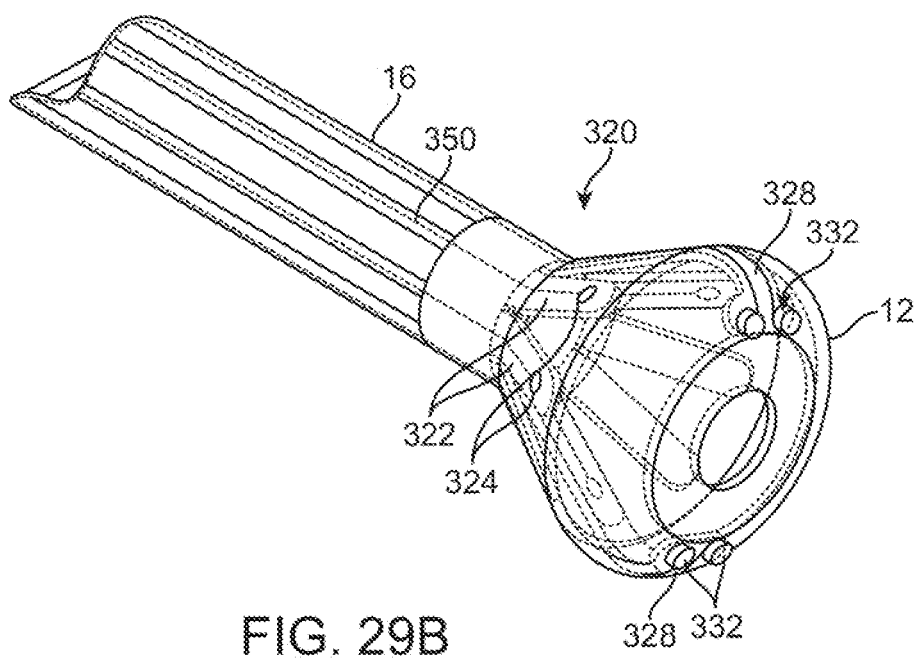

FIGS. 29A and 29B show perspective views of an exemplary hood with a flexible circuit assembly 320 integrated with the hood 12. As shown, one or more flexible circuit arm members 322 may extend distally upon or along the hood 12 in a radial pattern with conductive traces having optionally exposed electrodes 324 near the distal ends of the arm members 322. Each of the circuit arm members 322 may flare radially along with the hood structure and the one or more of the arm members 322 may also include distally extending circuit arm members 326 which may have a distal circuit portion 328 which extends at least partially upon the distal membrane of the hood 12. Each of the distal circuit portions 328 may extend upon the distal membrane into proximity with the aperture 42 and may serve a dual function. For instance, the distal circuit portion 328 may have one or more exposed electrodes 330 which may be placed into direct contact against the tissue surface, e.g., for detecting electrical activity of the tissue. Additionally, the distal circuit portion 328 may also serve to provide structural support to the aperture 42 such that distortion of the aperture 42 is prevented by the presence of the circuit portions 328 when contacted against the tissue for detection and/or for tissue treatment such as during ablation energy delivery through the aperture 42.

Although two opposed circuit portions 328 are shown in the examples, a single circuit portion 328 or three or more circuit portions 328 may be utilized, e.g., four circuit portions 328 in a uniform radial pattern positioned about aperture 42. Additionally, the exposed electrodes 330 positioned upon the distal circuit portions 328 may be recessed or flush with the surface of the portion 328 but in alternative examples, the electrodes 330 may form conductive projections 332 which extend distally for facilitating contact against the underlying tissue, as shown in FIG. 29B.

FIG. 29C shows a perspective view of a variation having four circuit arm members 334a, 334b, 334c, 334d extending from the proximal portion of hood 12 such that each arm member is uniformly positioned in a radial manner with respect to one another. The printed circuit assembly may have a supporting frame made of, e.g., Nitinol, to provide additional structural support to the circuit assembly in some variations while in other variations, the supporting frame may be omitted entirely and structural support of the printed circuit assembly may be provided entirely by the polymeric circuit assembly. Each of the arm members 334a, 334b, 334c, 334d may extend radially with hood 12 and curve at its distal end towards a longitudinal axis of the hood 12 such that a respective distal circuit portion 336a, 336b, 336c, 336d extends at least partially within or upon the distal membrane 40 of hood 12. Each portion of the arm members between each respective distal circuit portion may be optionally reduced in cross-sectional area to facilitate the delivery and deployment of the arm members and distal circuit portions along with the hood 12 in use. With each respective distal circuit portion extending at least partially upon the distal membrane, a respective electrode 338a, 338b, 338c, 338d may be positioned upon the distal circuit portion to extend distally from the distal circuit portion such that each electrode lies flush with or protrudes from the surface of the distal membrane 40 for contacting the underlying tissue.

With each arm member 334a, 334b, 334c, 334d integrated with the hood 12, the arm members may provide structural support to the hood 12 to help maintain its shape and configuration when deployed within the body and/or urged against the tissue surface. Moreover, the arm members may also help to maintain the shape of the hood 12 whether the purging fluid is flowed within the hood 12 or not. Additionally, each of the distal circuit portions 336a, 336b, 336c, 336d may be positioned along the distal membrane 40 such that each of the circuit portions are in proximity uniformly about aperture 42. As the distal membrane 40 is placed or urged against the tissue surface for visualization and/or treatment, the distal circuit portions may help to maintain a shape of the aperture 42 by providing for uniform structural support about the aperture 42 and thereby help to prevent its distortion such that the aperture 42 retains its circular configuration (or any selected configuration) despite movement or compression of the hood 12 relative to the tissue due to movement of the device or from tissue contraction. Maintenance of the aperture 42 shape during visualization and/or energy delivery through the purging fluid within the hood 12 may help to prevent distortion through the visual field of the underlying tissue and may also help to ensure even distribution of the conducted energy via the electrolytic fluid through the aperture 42.

Figure 29D:
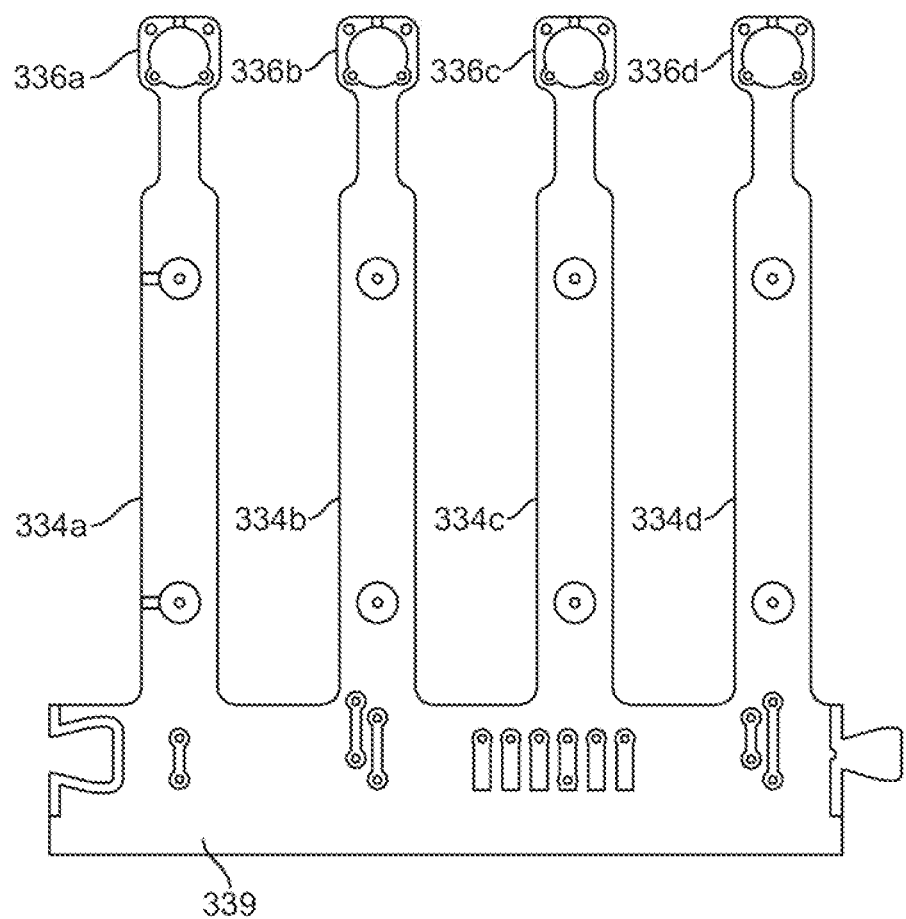
FIG. 29D shows a splayed view of a variation of the electrode array assembly.

A splayed view of another variation of the flexible circuit assembly having four arm members is shown in FIG. 29D. The printed circuit assembly, as previously mentioned, may be bonded to a Nitinol frame which may then be over-molded with silicone while in other variations, the Nitinol frame may be omitted entirely. The printed circuit assembly substrate may instead be stiffened to replicate the structural stiffness provided by a Nitinol frame. As shown in the figure, each of the arm member 334a, 334b, 334c, 334d may extend from a common support 339 which may be reconfigured into a circular structure for integration with the hood 12 such that each of the arm members extend longitudinally from the support 339 in a radial manner where each of the arm members are positioned to be in apposition from an opposed arm member about a circumference of the support 339.

Figure 30A:
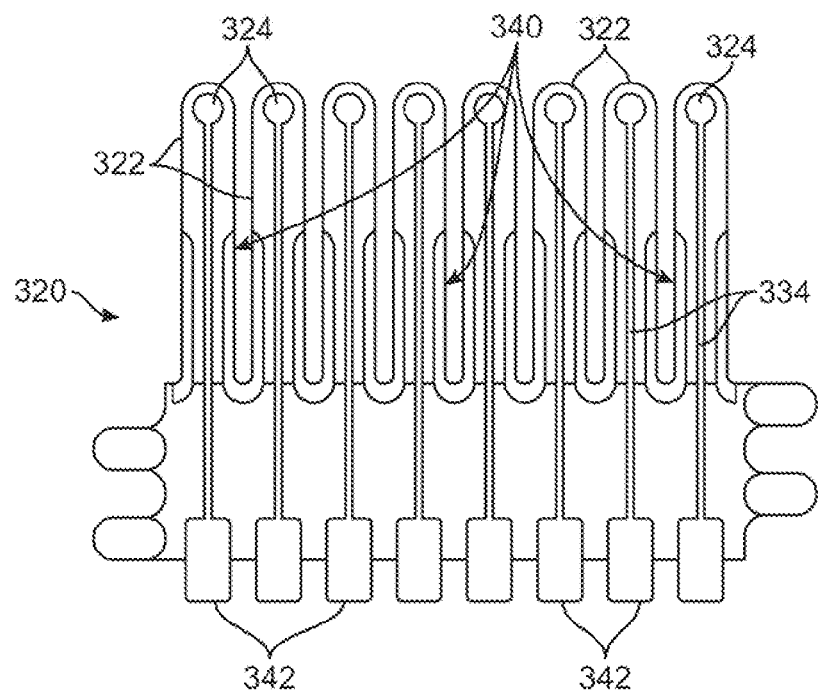
FIG. 30A shows an example of an electrode array assembly in a splayed configuration having one or more semi-rigid sections incorporated.
Figure 30B:
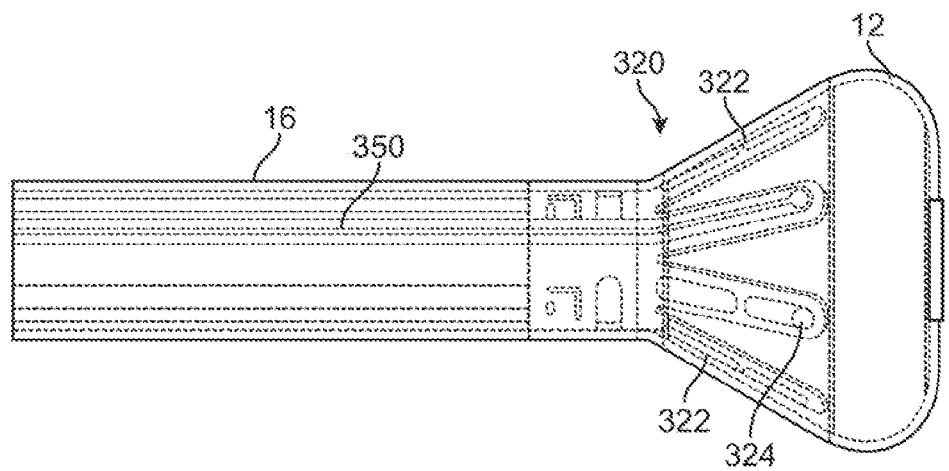
FIG. 30B shows a side view of the electrode array positioned upon the hood forming a semi-rigid frame structure.

FIG. 30A shows a splayed view of one example of a flexible circuit assembly 320 (formed via the methods described above) to have one or more circuit arm members 322 with exposed electrodes 324 positioned near the distal ends of each arm member 322. Each electrode 324 may be electrically connected via traces 344 to a corresponding conductive pad 342 defined near a proximal end of the circuit assembly 320 for connection to a conductor passing through the length of the catheter for electrical connection to a power source. FIG. 30B shows a side view of the flexible circuit assembly 320 integrated with the hood 12 and extending at least partially along the length of the hood 12. The exposed electrodes 324 may contact the purging electrolytic fluid introduced within the open area of the hood 12 for conducting electrical energy through the fluid and into the tissue through the aperture 42. Moreover, the flexible circuit assembly 320 may also provide structural support to the hood when formed into a circumferential configuration with each of the arms 322 extending radially along the hood 12 especially if provided with semi-rigid sections 340. These sections 340 may comprise portions of the arm members 322 reinforced with additional polymeric material around the regions (such as the radiused portions where the arm members 322 extend from the assembly 320) where the circuit assembly 320 flexes and bends, particularly during hood delivery and deployment.

Figure 31A:
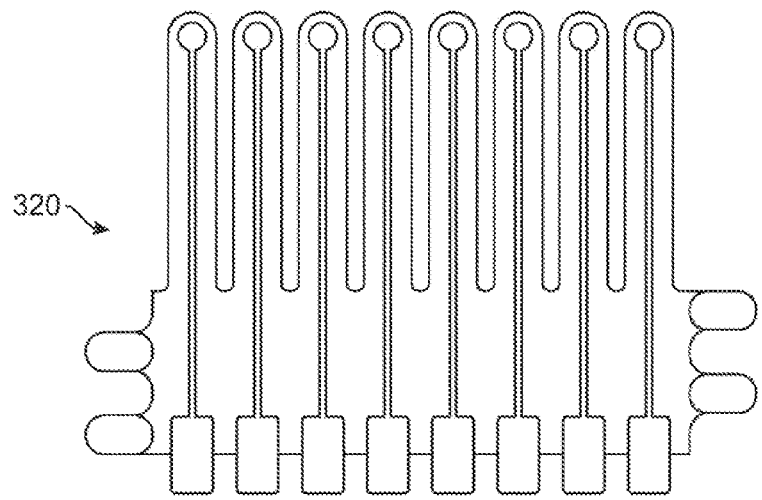
FIG. 31A shows an electrode array prior to assembly with the hood structure.
Figure 31B:
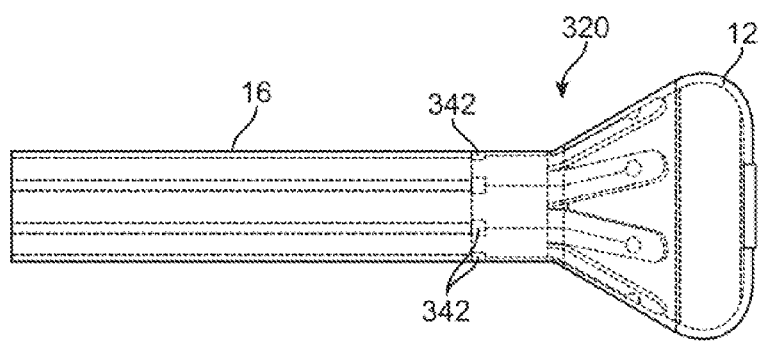
FIGS. 31B to 31D show side and perspective views of an assembled electrode array integrated within the hood structure.
Figure 31C:
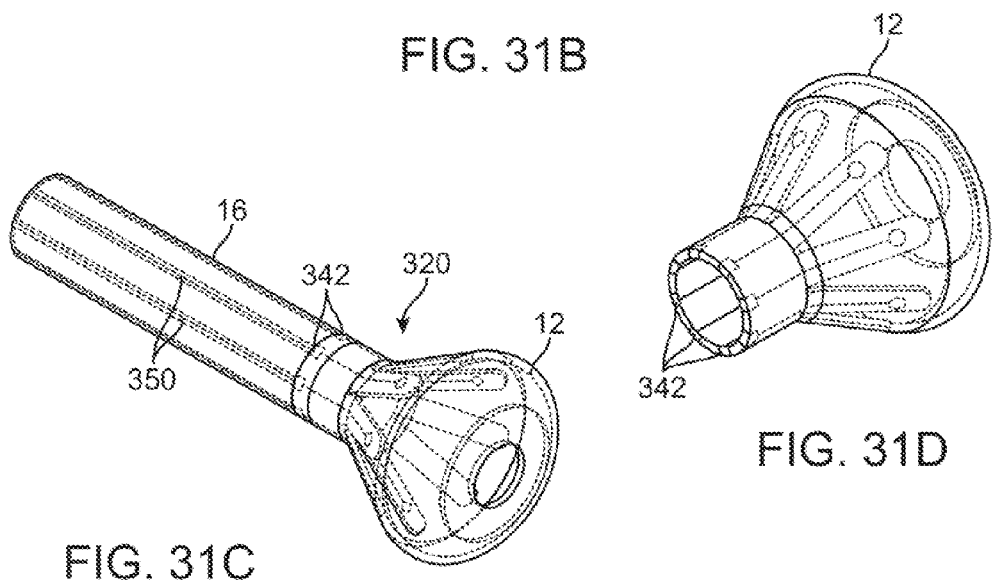
Figure 31D:
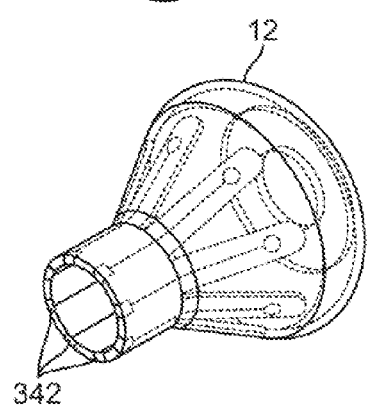

In addition to providing electrical contacts within the hood structure, these circuit assemblies also maintain electrical connectivity through the catheter 16 and to the proximal end of the catheter 16 to a power supply. FIG. 31A shows an exemplary circuit assembly 320 integrated with hood 12 and attached to the catheter 16 shown in FIG. 31B. Each of the conductive pads 342 located along the proximal end of the hood assembly, as shown in the perspective view of FIG. 31D, may come into electrical contact with a corresponding exposed conductive pad located near or at the distal end of the catheter 16 for bringing the electrode connections to the proximal end of the catheter via conductors 350 which may run the length of the catheter assembly, as shown in the side and perspective views of FIGS. 31B and 31C.

Figure 32A:
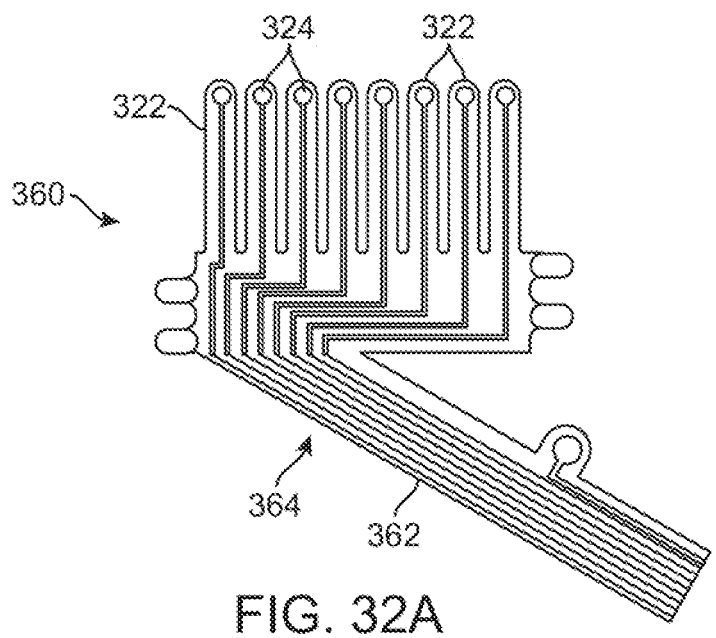
FIG. 32A shows another example of an electrode array in a splayed configuration.
Figure 32B:
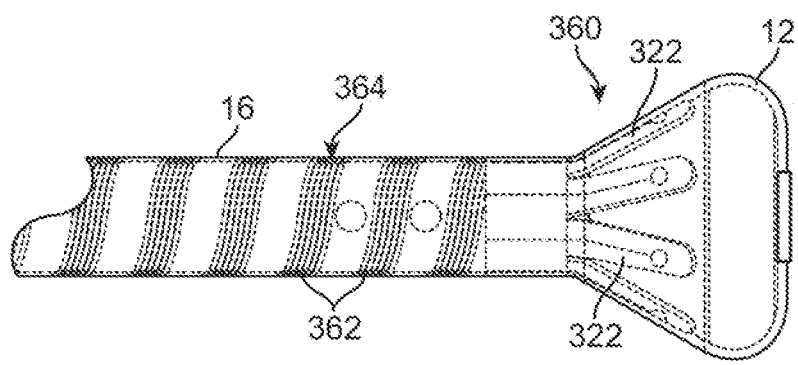
FIGS. 32B and 32C show side and perspective views of the electrode array assembled within the hood structure and having the conductors wrapped about the catheter shaft.
Figure 32C:
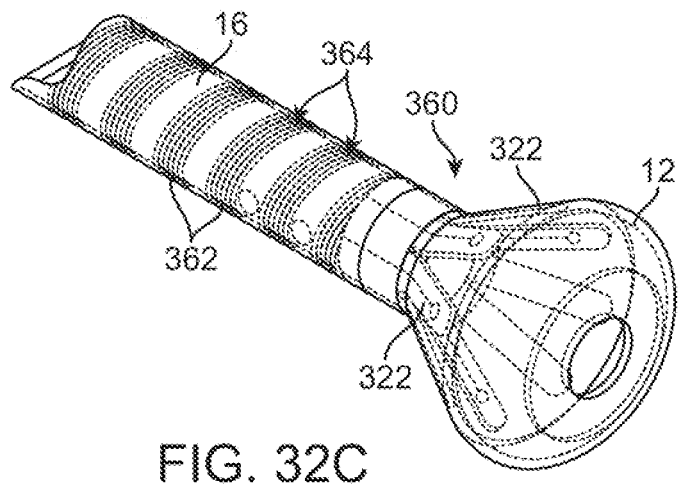

Conductors 350 may be parallel to the axis of the catheter 16 or they may be slightly inclined with respect to this axis so that it can be made to spiral along the shaft of the catheter 16. As shown in the splayed view of the circuit assembly 360 in FIG. 32A, a proximally extending circuit assembly 362 having one or more of the corresponding conductive traces 364 may be angled with respect to the circuit assembly 360 such that the proximally extending portion of the assembly 362 may be wrapped in a spiraling configuration as shown in the side and perspective views of FIGS. 32B and 32C. Such sections may also include exposed electrode pads to be used for purposes such as the determination of the location of the catheter body via electro-anatomical mapping. Moreover, such an assembly may also reduce the diameter of the catheter assembly.

The applications of the disclosed invention discussed above are not limited to devices used for treatments of tissue within the heart, but may include any number of other systems and treatments for use in different areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A tissue treatment assembly, comprising:
    an elongate catheter extending along a longitudinal axis and defining a fluid lumen therethrough, the elongate catheter terminating at a distal opening in communication with the fluid lumen;
    a fluid barrier projecting distally of the distal opening of the catheter and configurable between a low profile and a deployed profile, wherein in the deployed profile, the fluid barrier defines an open area in fluid communication with the distal opening of the catheter and includes a distal membrane extending in a plane that intersects the longitudinal axis, the distal membrane defining at least one aperture such that the open area is in communication with an environment external to the fluid barrier; and
    at least one arm member formed from a polymeric assembly extending distally along the fluid barrier and at least partially upon the distal membrane.

2. The assembly of claim 1 wherein the fluid barrier is comprised of a fluid impermeable membrane.

3. The assembly of claim 1 wherein the aperture defines a diameter of at least 2 mm or greater.

4. The assembly of claim 1 further comprising four arm members formed from the polymeric assembly and extending distally along the fluid barrier.

5. The assembly of claim 1 wherein the at least one arm members inhibits distortion of the aperture.

6. The assembly of claim 1 wherein the polymeric assembly comprises at least one electrode exposed from the fluid barrier.

7. The assembly of claim 6 wherein the polymeric assembly further comprises one or more conductive traces electrically coupled to the at least one electrode.

8. The assembly of claim 1 wherein the polymeric assembly comprises a flexible printed circuit assembly.

9. The assembly of claim 1 wherein the polymeric assembly is molded integrally with the fluid barrier.

10. The assembly of claim 1 wherein the polymeric assembly is formed from a plurality of polymeric layers.

11. The assembly of claim 1 wherein the polymeric assembly comprises rigidized portions which provide structural support during flexing or bending of the assembly.

* * * * *

UNITED STATES PATENT AND TRADEMARK OFFICE
CERTIFICATE OF CORRECTION

| | |
|---|---|
| PATENT NO. | : 8,894,643 B2 |
| APPLICATION NO. | : 12/778907 |
| DATED | : November 25, 2014 |
| INVENTOR(S) | : Jason Paul Watson et al. |

It is certified that error appears in the above-identified patent and that said Letters Patent is hereby corrected as shown below:

On the Title Page item (75)

Please correct the spelling of the first inventor's name as follows:

--John Paul WATSON-- should be Jason Paul WATSON

Signed and Sealed this
First Day of September, 2015

Michelle K. Lee
*Director of the United States Patent and Trademark Office*